US012611343B2

(12) United States Patent (10) Patent No.: US 12,611,343 B2
Remus et al. (45) Date of Patent: Apr. 28, 2026

(54) ABSORBENT ARTICLE PACKAGES WITH NATURAL FIBERS

(71) Applicant: The Procter & Gamble Company, Cincinnati, OH (US)

(72) Inventors: Michael Remus, Heidelberg (DE); Silke Basendowski, Hofheim am Taunus (DE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 18/437,286

(22) Filed: Feb. 9, 2024

(65) Prior Publication Data

US 2024/0269014 A1 Aug. 15, 2024

(30) Foreign Application Priority Data

Feb. 9, 2023 (EP) ..................................... 23155825

(51) Int. Cl.
*A61F 13/551* (2006.01)
(52) U.S. Cl.
CPC .... *A61F 13/5511* (2013.01); *A61F 13/55145* (2013.01)
(58) Field of Classification Search
CPC ............... A61F 3/55105; A61F 3/5511; A61F 13/55105; A61F 13/5511
USPC ........................................... 53/562; 206/440
See application file for complete search history.

(56) References Cited

U.S. PATENT DOCUMENTS

| | | | |
|---|---|---|---|
| 2,146,308 A | 2/1939 | Maxfield | |
| 2,290,564 A | 7/1942 | Krueger | |
| 2,821,337 A | 1/1958 | Morgan, Jr. | |
| 2,878,849 A * | 3/1959 | Lingenfelter | B65D 33/00 |
| | | | 156/203 |
| 3,312,339 A | 4/1967 | Million | |
| 3,319,538 A * | 5/1967 | Bodolay | B65B 9/093 |
| | | | 53/562 |

(Continued)

FOREIGN PATENT DOCUMENTS

| | | |
|---|---|---|
| EP | 0439209 A1 | 7/1991 |
| EP | 0450114 A1 | 10/1991 |

(Continued)

OTHER PUBLICATIONS

PCT Search Report and Written Opinion for PCT/US2024/010617 dated Jun. 7, 2024, 18 pages.

(Continued)

*Primary Examiner* — Gloria R Weeks
(74) *Attorney, Agent, or Firm* — Amanada Herman Berghauer; Anna Haller

(57) ABSTRACT

A package for one or more absorbent articles, a process for forming a package for absorbent articles, and a set comprising a trimmed package for absorbent articles and a trim piece are disclosed. The package includes a package material enclosing the one or more absorbent articles. The package material has natural fibers and forms a front panel, a back panel opposite the front panel, a first side panel, a second side panel opposite the first side panel, a top panel, and a bottom panel opposite the top panel. The panels define an interior compartment, in which the absorbent articles are disposed. The distance between a seal line and a top edge is equal to or larger than 65 mm.

17 Claims, 14 Drawing Sheets

(56)                References Cited

U.S. PATENT DOCUMENTS

| | | | |
|---|---|---|---|
| 3,462,026 A | | 8/1969 | MacCherone |
| 3,519,197 A | | 7/1970 | Campbell |
| 3,640,450 A | | 2/1972 | Lieberman |
| 3,686,823 A | * | 8/1972 | Perlman .................. B65D 31/00 53/434 |
| 3,741,778 A | | 6/1973 | Rowe |
| 3,791,573 A | * | 2/1974 | Titchenal ............. B65D 33/002 229/69 |
| 3,844,409 A | * | 10/1974 | Bodolay ................ B65D 31/12 206/466 |
| 3,979,049 A | | 9/1976 | Achelpohl |
| 4,290,467 A | * | 9/1981 | Schmidt .................. B65D 33/14 383/65 |
| 4,563,231 A | * | 1/1986 | Porrmann ........... B29C 66/8181 426/135 |
| 4,667,453 A | * | 5/1987 | Goglio .................. B29C 66/723 426/123 |
| 4,691,368 A | | 9/1987 | Roessiger |
| 4,878,580 A | * | 11/1989 | Johnston .............. B42D 15/045 206/459.5 |
| 4,969,310 A | * | 11/1990 | Lerner .................. B65B 43/267 53/384.1 |
| 4,988,332 A | | 1/1991 | Mattle |
| 5,065,868 A | * | 11/1991 | Cornelissen ........... B65D 33/02 206/83.5 |
| 5,091,229 A | * | 2/1992 | Golike .................. H01L 23/552 428/404 |
| 5,221,567 A | * | 6/1993 | Baker ..................... B31B 70/00 493/194 |
| 5,457,944 A | | 10/1995 | Lipes |
| 5,468,206 A | | 11/1995 | Buchanan |
| 5,474,818 A | * | 12/1995 | Ulrich ............... B65D 75/5855 428/34.3 |
| 5,509,915 A | | 4/1996 | Hanson |
| 5,830,118 A | | 11/1998 | Nicholson |
| 5,908,113 A | | 6/1999 | Takemasa et al. |
| 5,934,470 A | | 8/1999 | Bauer et al. |
| 6,033,112 A | | 3/2000 | Sorenson et al. |
| 6,214,392 B1 | * | 4/2001 | Ramirez ................ B65D 33/01 426/106 |
| 6,229,061 B1 | * | 5/2001 | Dragoo ................. A61F 13/493 604/385.14 |
| 6,446,796 B1 | | 9/2002 | Schmidt |
| 6,536,951 B1 | * | 3/2003 | Sill .......................... B29C 66/43 383/127 |
| 6,698,928 B2 | | 3/2004 | Miller |
| 6,761,013 B2 | * | 7/2004 | Tippey .................. B65D 85/07 53/429 |
| 6,823,650 B2 | * | 11/2004 | Recchia, Jr. ........ B29C 66/1122 53/415 |
| 6,881,287 B2 | * | 4/2005 | Yasuhira .............. B29C 66/232 156/308.4 |
| 6,938,394 B2 | * | 9/2005 | Perell .................. B65D 75/5855 53/450 |
| 7,004,320 B1 | | 2/2006 | Schmidt et al. |
| 7,147,630 B2 | * | 12/2006 | Takino .............. A61F 13/49001 604/385.01 |
| 7,448,185 B2 | * | 11/2008 | Zeedyk .................. B65B 61/12 53/469 |
| 7,721,887 B2 | | 5/2010 | Hancock-cooke et al. |
| 7,780,353 B2 | | 8/2010 | Yoffe |
| 8,074,801 B2 | | 12/2011 | Slayton et al. |
| 8,097,313 B2 | | 1/2012 | Wallat |
| 8,240,915 B2 | | 8/2012 | Sargin et al. |
| 8,348,916 B2 | | 1/2013 | Fujikawa et al. |
| 8,631,939 B2 | | 1/2014 | Benson et al. |
| 8,794,443 B2 | | 8/2014 | Ueda |
| 8,899,418 B2 | | 12/2014 | Francis |
| 8,978,346 B2 | * | 3/2015 | Breck .................... B32B 27/08 428/35.2 |
| 9,217,097 B2 | * | 12/2015 | Paleari .................. B32B 27/32 |
| 9,382,043 B2 | | 7/2016 | Rummo |
| 9,468,566 B2 | | 10/2016 | Rosati et al. |

| | | | |
|---|---|---|---|
| 9,878,839 B2 | | 1/2018 | Santos |
| 9,914,562 B2 | | 3/2018 | Fox et al. |
| 9,932,149 B2 | | 4/2018 | Puccini |
| 9,994,376 B2 | | 6/2018 | De Soto-burt et al. |
| 10,378,152 B2 | | 8/2019 | Kinast |
| 10,760,219 B2 | | 9/2020 | Niemi |
| 10,786,404 B2 | | 9/2020 | Cheng et al. |
| 11,396,170 B2 | | 7/2022 | Knauf et al. |
| 11,420,784 B2 | | 8/2022 | Parker et al. |
| 11,773,521 B2 | * | 10/2023 | Ashraf .................. A61F 13/551 428/156 |
| 11,794,976 B2 | | 10/2023 | Remus |
| 11,833,019 B2 | | 12/2023 | Remus et al. |
| 12,076,221 B2 | * | 9/2024 | Remus ................... B65D 75/12 |
| 12,090,034 B2 | * | 9/2024 | Remus ................... A61F 13/49 |
| 12,325,576 B2 | * | 6/2025 | Remus ................... A61F 13/551 |
| 2001/0056270 A1 | | 12/2001 | Mizutani et al. |
| 2002/0148749 A1 | | 10/2002 | Briseboi et al. |
| 2003/0106825 A1 | | 6/2003 | Molina et al. |
| 2003/0115837 A1 | * | 6/2003 | Zimmer ............. B65D 33/1691 53/399 |
| 2003/0157354 A1 | * | 8/2003 | Van Veghel ............. C08J 7/052 428/515 |
| 2004/0129592 A1 | * | 7/2004 | Otsubo ............. A61F 13/55115 206/440 |
| 2004/0232024 A1 | | 11/2004 | Guerreschi |
| 2004/0238393 A1 | | 12/2004 | Ohi et al. |
| 2004/0241359 A1 | | 12/2004 | Miksic et al. |
| 2005/0222550 A1 | * | 10/2005 | Mitsui .............. A61F 13/55115 206/440 |
| 2006/0051603 A1 | | 3/2006 | Cleveland et al. |
| 2006/0191985 A1 | | 8/2006 | Norcom |
| 2007/0031069 A1 | * | 2/2007 | Rabiea .................... A47F 9/042 383/106 |
| 2007/0099542 A1 | | 5/2007 | Sakaguchi et al. |
| 2007/0230834 A1 | | 10/2007 | Schneider |
| 2009/0084698 A1 | | 4/2009 | Ito et al. |
| 2009/0145792 A1 | | 6/2009 | Lewis |
| 2009/0157033 A1 | | 6/2009 | Toro et al. |
| 2009/0249751 A1 | | 10/2009 | Hyttel et al. |
| 2009/0279813 A1 | * | 11/2009 | Pokusa .................. B65D 33/20 383/211 |
| 2009/0281268 A1 | * | 11/2009 | Rukavina ............ B32B 17/1077 528/60 |
| 2010/0150479 A1 | | 6/2010 | Smith |
| 2010/0273377 A1 | | 10/2010 | Files et al. |
| 2011/0046591 A1 | | 2/2011 | Warner |
| 2011/0257616 A1 | | 10/2011 | Lakso et al. |
| 2012/0228182 A1 | * | 9/2012 | Ting ...................... B65D 65/42 428/319.3 |
| 2012/0288693 A1 | | 11/2012 | Stanley et al. |
| 2012/0305436 A1 | * | 12/2012 | Seyffer .................. D21H 21/16 206/524.6 |
| 2013/0046271 A1 | | 2/2013 | Pittet et al. |
| 2013/0156352 A1 | | 6/2013 | Koehn |
| 2013/0219830 A1 | * | 8/2013 | Nair ..................... B65D 75/522 53/452 |
| 2013/0220860 A1 | | 8/2013 | Bacon |
| 2013/0248398 A1 | * | 9/2013 | Harada ..................... B65B 9/06 206/440 |
| 2014/0319003 A1 | | 10/2014 | Hawighorst et al. |
| 2014/0348444 A1 | * | 11/2014 | Puccini .................. B65D 33/08 53/452 |
| 2014/0348445 A1 | | 11/2014 | Siesto Casanova et al. |
| 2015/0266663 A1 | | 9/2015 | Joseph |
| 2015/0298843 A1 | * | 10/2015 | Broeders ................ B29C 65/08 53/471 |
| 2015/0298861 A1 | * | 10/2015 | Dabadie .................. B32B 27/32 428/323 |
| 2016/0038628 A1 | | 2/2016 | Klofta et al. |
| 2016/0073689 A1 | * | 3/2016 | Sebastian .............. D04H 1/435 156/181 |
| 2017/0260694 A1 | | 9/2017 | Torniainen et al. |
| 2017/0274613 A1 | | 9/2017 | Stafford, III |
| 2017/0350074 A1 | | 12/2017 | Kinast |
| 2018/0187377 A1 | | 7/2018 | Ziegenbein |
| 2018/0289564 A1 | | 10/2018 | Sheehan |
| 2018/0304607 A1 | | 10/2018 | Öhman et al. |

(56) References Cited

U.S. PATENT DOCUMENTS

| | | | |
|---|---|---|---|
| 2018/0334292 A1 | 11/2018 | Tan | |
| 2019/0091077 A1 | 3/2019 | Cheng et al. | |
| 2019/0126603 A1 | 5/2019 | Zerial | |
| 2019/0135515 A1 | 5/2019 | Jasso | |
| 2020/0030162 A1 | 1/2020 | Lindner et al. | |
| 2020/0231365 A1 | 7/2020 | Veiseh | |
| 2020/0354129 A1 | 11/2020 | Sheehan et al. | |
| 2020/0368082 A1 | 11/2020 | Cheng et al. | |
| 2021/0043023 A1 | 2/2021 | Coder et al. | |
| 2021/0108371 A1 | 4/2021 | Oshima et al. | |
| 2021/0114789 A1 | 4/2021 | Kuiper et al. | |
| 2021/0221544 A1 | 7/2021 | Wallenius et al. | |
| 2022/0031531 A1 | 2/2022 | Remus et al. | |
| 2022/0031532 A1* | 2/2022 | Remus | A61F 13/551 |
| 2022/0031533 A1 | 2/2022 | Remus et al. | |
| 2022/0033159 A1 | 2/2022 | Remus et al. | |
| 2022/0034040 A1* | 2/2022 | Boswell | B32B 5/16 |
| 2022/0079819 A1 | 3/2022 | Houben et al. | |
| 2022/0110801 A1* | 4/2022 | Remus | B65D 85/07 |
| 2022/0110802 A1* | 4/2022 | Remus | A61F 13/5514 |
| 2022/0204234 A1 | 6/2022 | Chapjian | |
| 2022/0266563 A1 | 8/2022 | Schlarp et al. | |
| 2022/0362073 A1 | 11/2022 | Shimizu et al. | |
| 2023/0011142 A1 | 1/2023 | Yoshiba | |
| 2023/0036459 A1 | 2/2023 | Yoshiba | |
| 2023/0048153 A1 | 2/2023 | Remus et al. | |
| 2023/0060828 A1 | 3/2023 | Yoshiba | |
| 2023/0165737 A1* | 6/2023 | Remus | B65D 65/466 |
| | | | 206/494 |
| 2024/0148570 A1 | 5/2024 | Remus | |
| 2024/0245561 A1* | 7/2024 | Motsch | B65D 65/466 |

FOREIGN PATENT DOCUMENTS

| | | | |
|---|---|---|---|
| EP | 1291290 A1 | 3/2003 | |
| EP | 1618860 A1 | 1/2006 | |
| EP | 2276673 B1 | 1/2014 | |
| EP | 2730698 A1 | 5/2014 | |
| EP | 2796384 A1 | 10/2014 | |
| EP | 2704963 B1 | 9/2016 | |
| EP | 3561178 A1 | 10/2019 | |
| EP | 3575233 B1 | 3/2021 | |
| EP | 3643634 B1 | 7/2021 | |
| EP | 3865421 A1 | 8/2021 | |
| EP | 3954535 A1 | 2/2022 | |
| EP | 3901054 B1 | 8/2022 | |
| EP | 4070929 A1 | 10/2022 | |
| GB | 823855 A | 11/1959 | |
| GB | 829215 A | 3/1960 | |
| GB | 1520492 A | 8/1978 | |
| GB | 2545456 A | 6/2017 | |
| JP | S58160033 A | 9/1983 | |
| JP | H05168660 A | 7/1993 | |
| JP | 3094949 B2 | 10/2000 | |
| JP | 2003128081 A | 5/2003 | |
| JP | 2005145561 A | 6/2005 | |
| JP | 2007262603 A | 10/2007 | |
| JP | 2010222006 A | 10/2010 | |
| JP | 2014198588 A | 10/2014 | |
| JP | 2015227517 A | 12/2015 | |
| JP | 2017218157 A | 12/2017 | |
| KR | 20080111808 A | 12/2008 | |
| NZ | 264733 A | 4/1997 | |
| WO | 9210412 A1 | 6/1992 | |
| WO | 9723186 A1 | 7/1997 | |
| WO | 02094678 A1 | 11/2002 | |
| WO | 02096331 A2 | 12/2002 | |
| WO | 2004103841 A1 | 12/2004 | |
| WO | 2011073808 A2 | 6/2011 | |
| WO | 2013008938 A1 | 1/2013 | |
| WO | 2013160199 A1 | 10/2013 | |
| WO | 2015088037 A1 | 6/2015 | |
| WO | 2019056351 A1 | 3/2019 | |
| WO | 2020121160 A1 | 6/2020 | |
| WO | 2021165317 A1 | 8/2021 | |
| WO | 2021199600 A1 | 10/2021 | |
| WO | 2021200656 A1 | 10/2021 | |
| WO | 2021200657 A1 | 10/2021 | |
| WO | 2022022884 A1 | 2/2022 | |
| WO | 2022059324 A1 | 3/2022 | |
| WO | 2022129674 A1 | 6/2022 | |
| WO | 2022158102 A1 | 7/2022 | |
| WO | 2023117604 A1 | 6/2023 | |
| WO | 2023241810 A1 | 12/2023 | |
| WO | 2023241811 A1 | 12/2023 | |

OTHER PUBLICATIONS

"Aegis Paper", Online retrieved from "https://www.nspackaging. com/news/mondi-aegispaper-barrier/";2021; 02 pages.

"Axello Tough White White MF Kraft Paper", Online retrieved from "https://www.billerudkorsnas.com/packaging-materials/kraft-paper-bags/axello",2019, 01 page.

"Kraft paper", Online retrieved from "https://en.wikipedia.org/wiki/ Kraft_paper"; Unknown date;03 pages.

"Wax Paper", Online retrieved from "https://en.wikipedia.org/wiki/ Waxed_paper"; Unknown date; 02 pages.

Axello Tough White White MF Kraft Paper. Specification Data [online]. BillerudKorsnas Axello, Sep. 12, 2019 [retrieved on Sep. 22, 2022]. Retrieved from the Internet :https://www.billerudkorsnas. com/packaging-materials/kraft-paper-bags/axello (Year:2019), 12 pages.

EPO Search Report and Opinion for Application No. 23155825.5; dated Oct. 11, 2023, 12 pages.

Jonathan Fowle et al. "Paper-based flexible packaging", 2003, pp. 91-123.

Mark J. Kirwan, "Paper and Paperboard Packaging Technology ", Available on https://www.booksfree.org/wp-content/uploads/2022/ 02/paper_and_paperboard_packaging_technology-signed.pdf, 2005, pp. 453.

Mespack Horizontal pouch machine, Available on https://www. youtube.com/watch?v=J6FKMopcMN8.

Mespack Innovative Packaging Technologies, Available on https:// www.e-morenos.com/wp-content/uploads/2017/06/NOU_cataleg_ general_ENG.pdf, No Known Date, pp. 48.

Richard Coles et al. "Food Packaging Technology", available on https://kasianparto.ir/wp-content/uploads/2022/03/Food-Packaging-Technology.pdf, vol. 5, 2003, pp. 362.

Thorsten Schmidt et al. "Reliability of evaluations for the choice of system solutions at the example of automated order picking systems for bagged goods", May 30, 2014, pp. 14.

* cited by examiner

4400

4400

4300

4100

4300

4000

4200

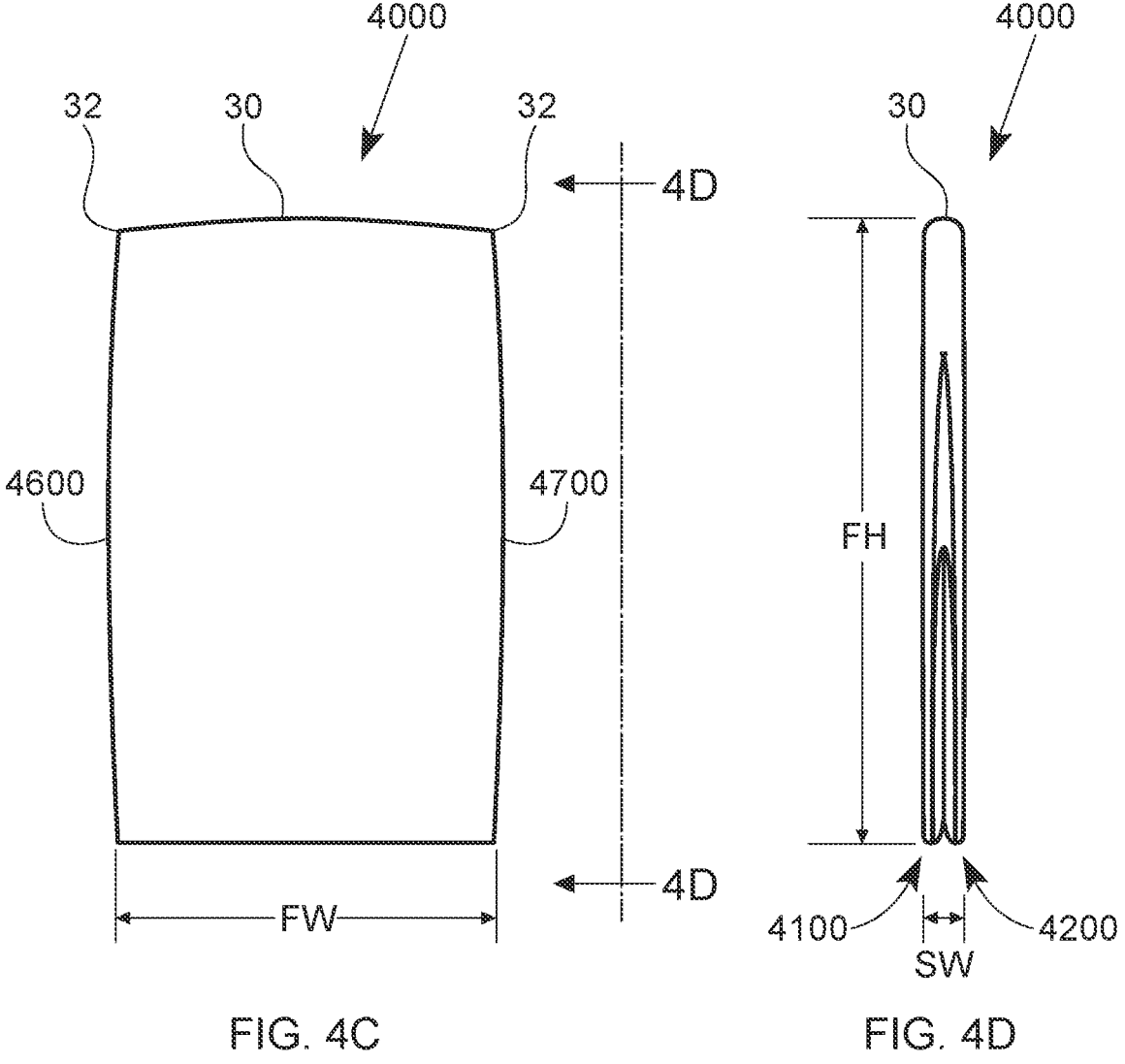
FIG. 4C                    FIG. 4D

ABSORBENT ARTICLE PACKAGES WITH NATURAL FIBERS

CROSS-REFERENCE TO RELATED CASES

This application claims priority under 35 U.S.C. § 119 to European Patent Application Serial No. EP 23155825.5, filed on Feb. 9, 2023, the entire disclosure of which is hereby incorporated by reference.

FIELD OF THE INVENTION

The present disclosure is directed to absorbent article packages, more particularly to absorbent article packages with natural fibers.

BACKGROUND

Consumer demand for products made at least partially from renewable resources has increased significantly over the past decade, and has become a driver of innovation for new and improved consumer goods and packaging materials. As such, there is an increased focus on products and packaging materials comprising renewable resources. For example, there is a strong desire in the marketplace for consumer products that comprise natural and bio-sourced materials, recyclable materials, recycled materials, and/or biodegradable materials.

Non-fragile, compressible consumer products such as disposable absorbent articles (e.g., diapers and training pants, disposable adult incontinence pants and feminine hygiene pads) are often packaged and sold at retail in soft packages formed of plastic polymer film. Plastic is preferred as the primary package of consumer goods because plastic may withstand the rigors of a packaging process, given plastic's ability to flex and stretch.

Packages comprising renewable resources, such as natural fibers (e.g., carton board, cardboard, and paper), may be prone to creasing, cracking, and tearing under packaging processes and opening strain. Further, existing packaging lines should be adapted to process packages comprising renewable resources with only minor adaptations.

Bags for disposable absorbent articles formed of plastic polymer films are typically provided to packaging lines in stacks of multiple bags. The individual bags comprise wicket holes to allow for support of the stack and alignment of the bags via wicket pins. After disposing the absorbent articles into the bags, the packages are typically sealed and the protruding material section comprising the wicket holes is trimmed. The trim is typically removed from the packaging line via suction means. Replacing the plastic polymer material by materials from renewable resources on existing packaging lines gives rise to challenges: Bags from renewable materials are typically thicker than polymer film bags in a flat laid-out state, thus a stack of the same height provided to the line comprises less bags. Further, the basis weight of materials from renewable sources is typically higher than a polymer film providing the same tensile and barrier properties. The increased weight/area ratio of trim complicates the removal from the line.

Net there is a need for packages comprising renewable resources which can be produced without or with only minor adaptations of existing packaging lines and can be supplied to lines in large quantities and without interruptions due to changing the supply stack.

SUMMARY

The present disclosure solves one or more of the problems discussed above by providing a package for absorbent articles. The package comprises a package material comprising natural fibers. The package material forms a bag having a first side edge, a second side edge opposite the first side edge, a top edge, and a bottom edge opposite the top edge in a flat laid-out state. The first side edge and second side edge are substantially parallel. The top edge and bottom edge are substantially parallel. The first side edge and second side edge are substantially rectangular to the top edge and bottom edge in a flat laid-out state. The bag with one or more absorbent articles disposed therein forms the package. The package is sealed along a seal line such that the one or more absorbent articles are enclosed within an interior compartment of the bag. The seal line on a front surface of the bag is substantially parallel to the bottom edge of the bag in a flat laid-out state. Length $L_S$ is the distance between the seal line and the top edge along a direction parallel to the first side edge of the bag in a flat laid-out state. $L_S$ is equal to or larger than 65 mm.

Further, a process for forming a package for absorbent articles is provided. The process comprises the steps of:

a) providing a package material comprising natural fibers forming a bag having a first side edge, a second side edge opposite the first side edge, a top edge, and a bottom edge opposite the top edge in a flat laid-out state; the first side edge and second side edge are substantially parallel, the top edge and bottom edge are substantially parallel and the first side edge and second side edge are substantially rectangular to the top edge and bottom edge in a flat laid-out state; and having an inside facing surface and an outside facing surface, wherein the inside facing surface comprises a scalable material;

b) disposing one or more absorbent articles through an open end located at the top edge to the bag to form a package with an interior compartment defined by a front panel, a back panel opposite the front panel, a first side panel, a second side panel opposite the first side panel, a top panel, and a bottom panel opposite the top panel formed by the package material;

c) sealing the package along a seal line such that the one or more absorbent articles are enclosed within the interior compartment, wherein the seal line on a front surface of the bag is substantially parallel to the bottom edge of the bag in a flat laid-out state; wherein length $L_S$ is the distance between the seal line and the top edge along a direction parallel to the first side edge of the bag in a flat laid-out state;

wherein $L_S$ is equal to or larger than 65 mm;

d) cutting the package along a trim line, which is located between the seal line and the top edge and is substantially parallel to the seal line;

c) removing the trim corresponding to the cut part.

Further a set comprising a trimmed package for absorbent articles and a trim piece is provided. The trimmed package comprises a package material comprising natural fibers. The trim piece comprises a trim material which is identical to the package material. The package material forms a front panel, a back panel opposite the front panel, a first side panel, a second side panel opposite the first side panel, a top panel, and a bottom panel opposite the top panel, wherein the panels define an interior compartment of the package, and wherein one or more absorbent articles are disposed in the interior compartment. The trimmed package is sealed along a seal line such that the one or more absorbent articles are enclosed within the interior compartment. The seal line is substantially parallel to the bottom edge, which is the edge between the front panel and the bottom panel, of the trimmed package. The trim material forms a trim material piece having a first side edge, a second side edge opposite the first side edge, a top edge, and a bottom edge opposite the top edge in a flat laid-out state; the first side edge and second side edge are substantially parallel, the top edge and bottom edge are substantially parallel and the first side edge and second side edge are substantially rectangular to the top edge and bottom edge in a flat laid-out state. The trim material piece has openings on the top and bottom edge. $L_{TP}$ is the distance between the top edge and the bottom edge along a direction parallel to the first side edge of the trim material piece in a flat laid-out state. $L_{TP}$ is equal to or larger than 55 mm.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 4C is a plan view of the diaper of FIG. 4B, shown folded about a lateral fold line, wearer-facing surfaces in and outward-facing surfaces out;

FIG. 4D is a side view of the folded diaper shown in FIG. 4C;

DETAILED DESCRIPTION

The term "absorbent article," as used herein, refers to devices which absorb and contain exudates, and, more specifically, refers to devices which are placed against or in proximity to the body of the wearer to absorb and contain the various exudates discharged from the body. Absorbent articles of the present disclosure include, but are not limited to, diapers, adult incontinence briefs, training pants, diaper holders, menstrual pads, incontinence pads, liners, absorbent inserts, pantiliners, tampons, and the like.

Figure 2:
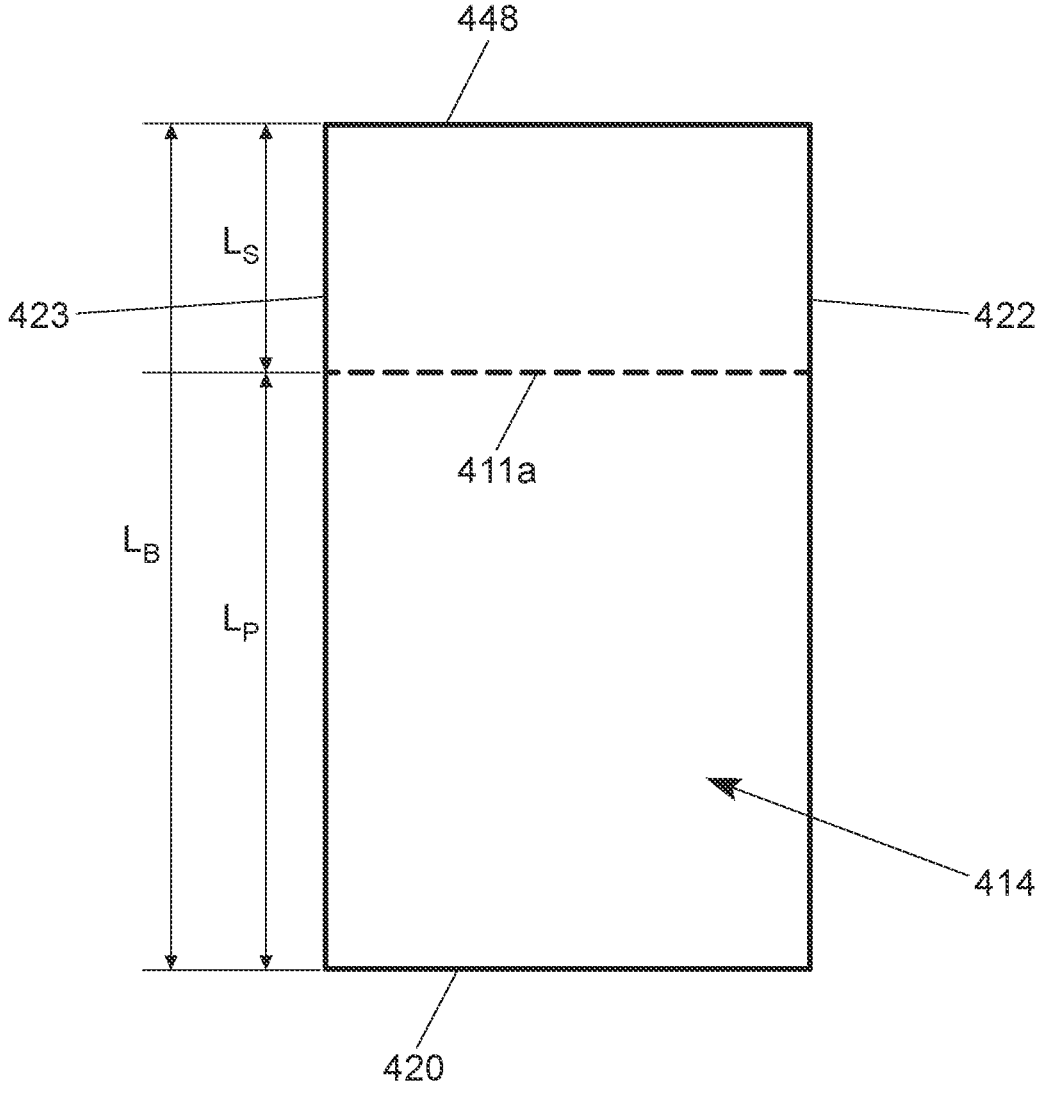
FIG. 2 is a plan view on the front surface of a bag in flat laid-out state.
Figure 2A:
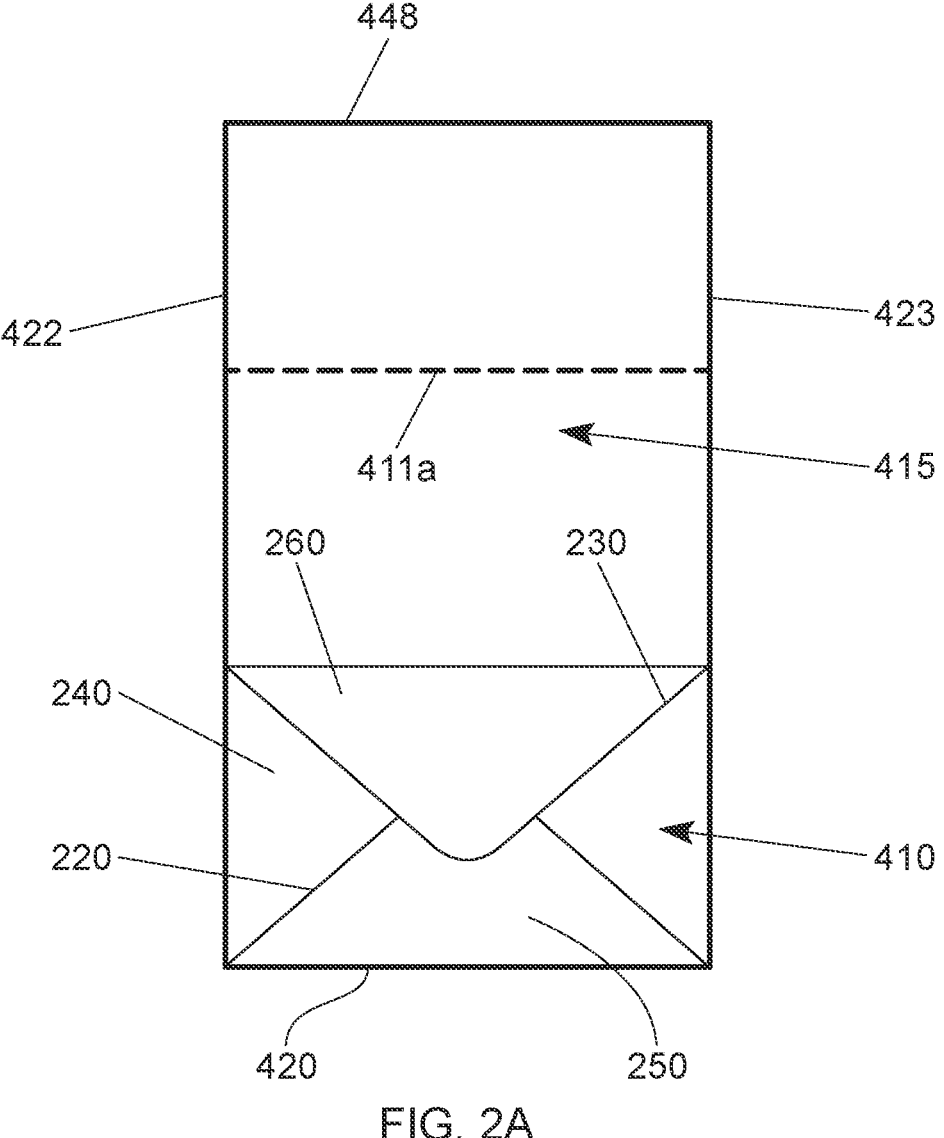
FIG. 2A is a plan view on the back surface of a bag in flat laid-out state with the bottom surface comprising seals in a block style configuration and being folded onto the back surface.
Figure 2B:
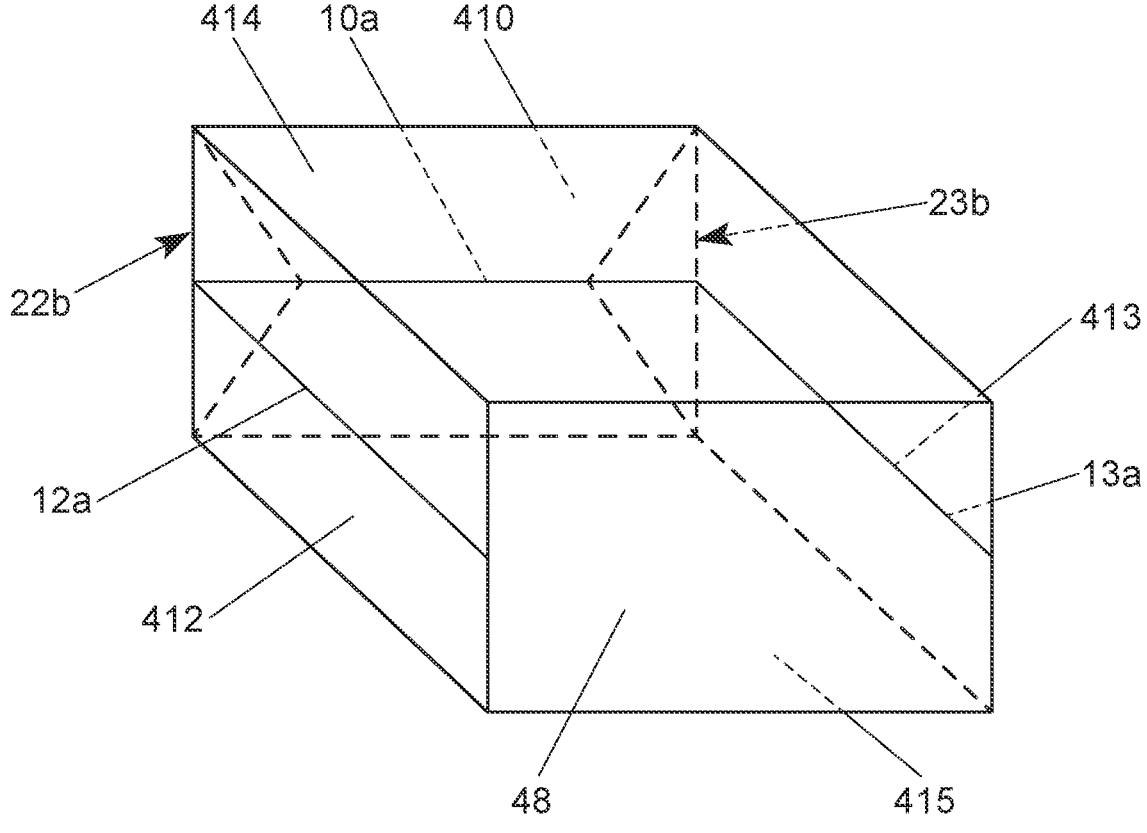
FIG. 2B is a schematic representation showing a bag, wherein the bottom surface of the bag comprises seals in a pinch bottom configuration.
Figure 2C:
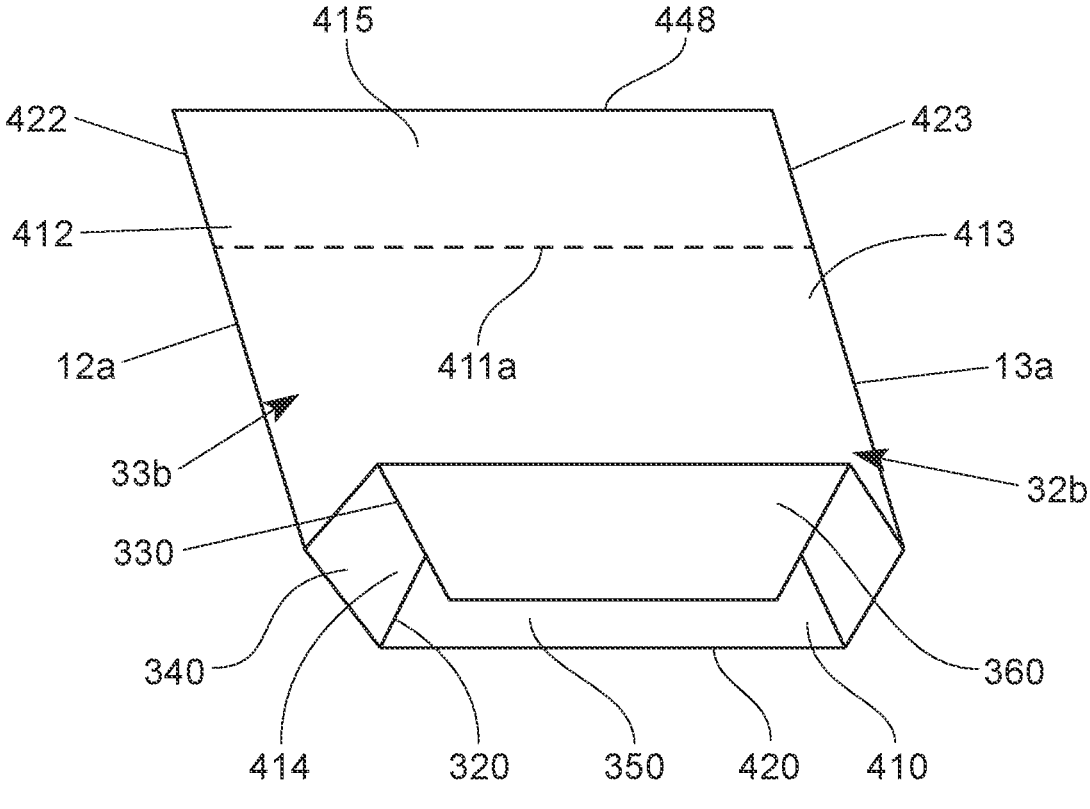
FIG. 2C is a schematic representation showing a bag flat laid-out state, wherein the bottom surface of the bag comprises seals in a cross style configuration.

The term "edge," as used herein, refers to the outermost boarder line of a bag, a package or a trim piece. Side edges are a straight line for at least part of the respective longitudinal length of the object. Side edges can preferably be substantially parallel to a longitudinal center line. Top and bottom edges are a straight line for at least part of the respective transversal width of the object. Top and bottom edges can preferably be substantially parallel to a transversal center line. A side edge can be a straight line for the entire longitudinal length of the object. Top and bottom edge can be a straight line for the entire transversal width of the object. The two side edges, and the top and the bottom edge can form a closed rectangle in a plan view. An example is shown in FIG. 2 and FIG. 2A. The two side edges can also be connected to the top and/or the bottom edge via straight connecting lines having an interior angle of less than 90°, in particular between 40° and 60°, to the side edge and top and/or the bottom edge. An example is shown in FIG. 2C. The two side edges can also be connected to the top and/or the bottom edge via curved or other non-linear connecting lines. Thus, chamfered corners can be formed between the side edge and top and/or the bottom edge. The corners between the respective side edges and the bottom edge may preferably be axial symmetric around the longitudinal center line. The corners between the respective side edges and the top edge may preferably be axial symmetric around the longitudinal center line.

The term "flat laid-out state", as used herein, refers to the bag or package in an empty state, i.e., without any product such as absorbent articles disposed therein, and the bag or package is laid out in a flat folded configuration, e.g., the side surfaces of the bag, the side panels of the package respectively are folded inwards or outwards and the front and back surface, the front and back panel respectively are in direct contact and/or with a minimized space in between.

The term "machine direction" or "MD," as used herein, refers to a path that material, such as a package material, follows through a manufacturing process.

The term "cross-machine direction" or "CD," as used herein, refers to a path that is perpendicular to the machine direction in the plane of the material.

The term "natural fibers" as used herein, refers to fibers which comprise cellulose-based fibers, bamboo fibers, and the like. Natural fibers also refers to: nonwoody fibers, such as cotton, abaca, kenaf, sabai grass, flax, esparto grass, straw, jute, hemp, bagasse, milkweed floss fibers, and pineapple leaf fibers; and woody fibers, such as wood or pulp fibers such as those obtained from deciduous and coniferous trees, including softwood fibers, such as northern and southern softwood kraft fibers, hardwood fibers, such as eucalyptus, maple, birch, and aspen. Pulp fibers may be prepared in high-yield or low-yield forms and may be pulped in any known method, including kraft, sulfite, high-yield pulping methods and other known pulping methods. The natural fibers of the present disclosure may be recycled natural fibers, virgin natural fibers or mixes thereof. Additionally, for good mechanical properties in natural fibers, it may be desirable that the natural fibers be relatively undamaged and largely unrefined or only lightly refined. The fibers may have a Canadian Standard Freeness of at least 200, more specifically at least 300, more specifically still at least 400, and most specifically at least 500.

The term "cellulose-based fibers," as used herein, may include regenerated cellulose fiber such rayon or cuprammonium rayon, and high pulping yield fibers, unless specified differently. The term "cellulose-based fibers" also includes chemically treated natural fibers, such as mercerized pulps, chemically stiffened or crosslinked fibers, or sulfonated fibers. Also included are mercerized natural fibers, regenerated natural cellulosic fibers, cellulose produced by microbes, the rayon process, cellulose dissolution and coagulation spinning processes, and other cellulosic material or cellulosic derivatives. Other cellulose-based fibers included are paper broke or recycled fibers and high yield pulp fibers. High yield pulp fibers are those fibers produced by pulping processes providing a yield of about 65% or greater, more specifically about 75% or greater, and still more specifically about 75% to about 95%. Yield is the resulting amount of processed fibers expressed as a percentage of the initial wood mass. Such pulping processes include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which leave the resulting fibers with high levels of lignin but are still considered to be natural fibers. High yield fibers are well known for their stiffness in both dry and wet states relative to typical chemically pulped fibers.

The package of the present disclosure comprises a package material containing absorbent articles wherein the package material comprises or is derived from natural resources. Namely, the package material of the present disclosure comprises natural fibers. The natural fibers may form a paper from which the package material is made. The composition of the package materials is discussed in additional detail herein.

Package Materials

The package materials of the present disclosure comprise natural fibers. The package materials of the present disclosure may comprise wood fiber and/or pulp fiber. The package materials may comprise at least 50 percent by weight natural fibers, at least 70 percent by weight natural fibers, at least 90 percent by weight natural fibers, between about 50 percent and about 100 percent by weight natural fibers, between about 65 percent and about 99 percent by weight natural fibers, or between about 75 percent and about 95 percent by weight of natural fibers, specifically reciting all values within these ranges and any ranges formed therein or thereby. In one form, the package materials may comprise 99.9% percent by weight natural fibers.

Inks and/or dyes associated with the package art, branding, package information, and/or background color, as well as adhesives associated with the seams and barrier coatings are also considered part of the package materials on a weight percentage basis. Where the weight percentage of natural fibers is less than 100 percent, the difference may be made up by inks, dyes, and/or adhesives. Inks, dyes, coatings, and adhesives may be considered contaminants in a paper recycling process, but may be otherwise recyclable.

While the package materials may comprise many different fibers, inks, dyes, coatings, adhesives, etc., the package material of the present disclosure may be constructed to facilitate and/or encourage recycling of the package material, and may encourage recycling of the package material within a single recycling stream, such as a paper recycling stream. Whether package materials are recyclable may vary from region to region. In order to meet one of the highest standards for recyclability, the total weight percentage of non-recyclable material, including material not recyclable within a particular recycling stream—such as a paper recycling stream—but otherwise recyclable, e.g., inks, dyes, adhesives, and coatings in the package material may be 5 percent by weight of the package material or less, or between 0.1 percent to 5 percent by weight, specifically reciting all values within these ranges and any ranges formed therein. However, other jurisdictions may allow a higher weight percentage of non-recyclable material. For example, in other jurisdictions, the package material of the present disclosure may comprise 50 percent by weight or less, 30 percent by weight or less, or about 15 percent by weight or less of non-recyclable material, specifically including all values within these ranges and any ranges formed therein or thereby. As another example, the package materials of the present disclosure may comprise from between about 0.1 percent to about 50 percent by weight, from about 0.1 percent to about 30 percent by weight, or from about 0.1 percent to about 15 percent by weight of non-recyclable material, specifically including all values within these ranges and any ranges formed therein or thereby. In an example, the amount of inks, dyes, coatings, and/or adhesives is 5 percent by weight, or less, or between 0.1 percent by weight to 5 percent by weight, specifically reciting all values within these ranges and any ranges formed therein.

The package materials of the present disclosure may be free of a barrier layer. As used herein, the term "barrier layer" refers to a layer of material, including barrier coatings, barrier plastics, and/or barrier foils, that is joined to the package materials comprising natural fibers. Such barrier layers may reduce the recyclability of the package materials within a single recycling stream.

In other instances, in order to at least partially protect absorbent articles disposed within the package, the package materials of the present disclosure may comprise a barrier layer. The barrier layer may at least partially inhibit the migration of water vapor through the package material. The barrier layer may comprise a water soluble material that may not interfere with a recycling process. The barrier layer may be easily separable from the remainder of the package materials through a recycling process, for example by having a different water solubility, density, buoyancy, or other physical features as compared to the remainder of the package materials.

The type of adhesives utilized for the seals of the packages of the present disclosure may impact the recyclability of the package as well. As an example, adhesives that can dissolve in water during the re-pulping step or the disintegration step of the paper recycling process may be particularly suitable for the packages of the present disclosure. Such adhesives include starch based adhesives, polyvinyl acetate based adhesives, and polyethylene oxide based adhesives. A suitable example of a starch based adhesive is available from LD Davis located in Monroe, North Carolina, under the trade name AP0420CR. A suitable example of a polyvinyl acetate based adhesive is available from Sekisui Chemical Company, located in Osaka, Japan, under the trade name Selvol 205. A suitable example of a polyethylene oxide based adhesive is available from Dow Chemicals Co. located in Midland, Michigan, under the trade name WSR N-80.

Water-dispersible adhesives may similarly be utilized. Suitable examples of water dispersible adhesives include thermoplastic elastomer based adhesives and polyvinyl acetate based adhesives. A suitable example of a thermoplastic elastomer based adhesive is available from Actega located in Blue Ash, Ohio, under the trade name Yunico 491. A suitable example of a polyvinyl acetate based adhesive is available from Bostik located in Milwaukee, Wisconsin, under the trade name Aquagrip 4419U01. Another suitable example of a polyvinyl acetate based adhesive is available from HB Fuller under the trade name PD-0330.

Without wishing to be bound by theory, it is believed that packages of the present disclosure which utilize adhesives dissolvable in water may comprise a higher weight percentage of such adhesives than adhesive which are only water dispersible. For example, packages comprising water dissolvable adhesives may comprise a first weight percentage of adhesive while packages comprising water dispersible adhesives may comprise a second weight percentage of adhesive. The first weight percentage may be greater than the second weight percentage for the purposes of recycling the package material.

Where a barrier layer is utilized, the barrier material may be selected such that the use of adhesives can be reduced or eliminated. One such barrier material may be polyethylene film coated on an inner surface of the package material. The polyethylene may be utilized to form the seals rather than an adhesive or in conjunction with an adhesive. However, as the polyethylene film may not be recyclable in the same stream as the other package materials, the weight percentage of the polyethylene may be in accordance with the present description regarding percentages of non-recyclable material discussed herein.

The effectiveness of the recycling process on the package material of the present disclosure may be determined via recyclable percentage. Package material of the present disclosure may exhibit recyclable percentages of 60 percent or greater, 75 percent or greater, or 90 percent or greater, specifically reciting all values within these ranges and any ranges formed therein or thereby. The packaging material of the present disclosure may have a recyclable percentage of between about 60 percent and about 99.9 percent, between about 75 percent and about 99.9 percent, or between about 90 percent and about 99.9 percent, specifically reciting all values within these ranges and any ranges formed therein or thereby. In a specific example, the package material of the present disclosure may exhibit a recyclable percentage of between about 95 percent and about 99.9 percent, specifically including all values within these ranges and any ranges formed therein. The recyclable percentage of the package material of the present disclosure is determined via test PTS-RH:021/97 (Draft October 2019) under category II, as performed by Papiertechnische Stiftung located at Pirnaer Strasse 37, 01809 Heidenau, Germany.

Along with recyclable percentage, the total reject percentage is determined via the PTS-RH:021/97 (Draft October 2019) under category II Test Method. The total reject percentage of the package material of the present disclosure may be 40 percent or less, 30 percent or less, or 10 percent or less, specifically including all values within these ranges and any ranges formed therein or thereby. For example, the total rejection percentage of the package material of the present disclosure may be from about 0.5 percent to about 40 percent, from about 0.5 percent to about 30 percent, or from about 0.5 percent to about 10 percent, specifically reciting all values within these ranges and any ranges formed therein or thereby.

It is believed that the percent non-recyclable material does not necessarily have a 1:1 correlation to the total reject percentage. For example, dissolvable adhesives and/or coatings are designed to dissolve during the recycling process. It is theorized that these adhesives may not have an impact the total reject percentage; however, they would contribute to the non-recyclable material weight percent.

The PTS-RH:021/97 (Draft October 2019) under category II Test Method also comprises a visual component. Trained screeners inspect one or more handsheets of recycled package material for visual imperfections. If the number of visual imperfections is too great, then the package material is rejected. If the number of visual imperfections is acceptable, in accordance with the PTS-RH:021/97 (Draft October 2019) under category II Test Method, then the package material is approved for additional processing. The package material of the present disclosure may yield an acceptable level of visual imperfections during this step of the method.

The package material of the present disclosure may yield the recyclable percentages mentioned heretofore as well as pass the visual screening method. Thus, the package material of the present disclosure may achieve an overall score or final outcome of "pass" when subjected to the PTS-RH:021/97 (Draft October 2019) under category II Test Method.

It is also worth noting that there is an alternative method for determining the recyclable percentage of the package material of the present disclosure. The Test Method performed by the University of Western Michigan, called the Repulpability Test Method, may provide a percent yield of recyclable material. While there are subtle differences between the Repulpability Test Method performed by Western Michigan and the PTS-RH:021/97 (Draft October 2019) under category II Test Method, it is believed that the percentage yield of the Repulpability Test Method would be similar to the recyclable percentage provided by the PTS Test Method.

It is contemplated that the package material of the present disclosure, while being recyclable, may itself comprise recycled material. Such determination can be made from a visual inspection of the package. For example, manufacturers typically advertise the use of recycled materials in an effort to demonstrate their eco-friendly product approach. To further expand on this example, some manufacturers may utilize a logo, e.g., a leaf, along with wording to indicate the use of recycled material in the package material. Often times, manufacturers may specify the percentage of recycled material utilized as well, e.g., over 50 percent, over 70 percent, etc.

Visual inspection may be as simple as utilizing the human eye to inspect packages for logos of the use of recycled material. Additionally, or alternatively, visual inspection may include microscopy methods such as optical microscopy, scanning electron microscopy or other suitable methods known in the art. For example, package material comprising recycled paper fibers may appear different under a microscope due to the presence of a much wider range of natural fiber types than if the package material comprised of 100% non-recycled paper. As another example, under a microscope, recycled fibers—due to their increased processing—may appear more fibrillated than their virgin fiber counterparts.

In order to withstand the rigors of a high speed manufacturing process where a plurality of absorbent articles are placed within the package, withstand the force of compressed absorbent articles being placed directly into the package without an intermediate package or container, withstand the rigors of being shipped, provide protection from environmental insults during shipping and while on the store shelf, and provide for product protection while in the consumers home, the package materials may have some level of strength, stretch, and/or resilience. The package materials of the present disclosure may be characterized using metrics such as: MD Tensile Strength in kN/m, CD Tensile Strength in kN/m, MD Stretch At Break in percent, CD Stretch At Break in percent, Burst Strength in kPa, Caliper in μm, MD Tensile Energy Absorption in $J/m^2$, CD Tensile Energy Absorption in $J/m^2$, and Basis Weight in grams per square meter. While all of the metrics may be utilized together to characterize the package materials of the present disclosure, it is believed that some of the metrics alone or in conjunction with others may suffice to characterize package materials which are suitable for packaging absorbent articles. As an example, it is believed that the Burst Strength may be utilized alone or in conjunction with other metrics to obtain package materials which are sufficient for packaging of absorbent articles. Similarly, it is believed that the Tensile Energy Absorption (TEA) in the MD and CD may be utilized in conjunction with one another, and if desired, along with any other combination of the above metrics, to obtain package materials which are suitable for packaging of absorbent articles. As yet another example, it is contemplated that MD Stretch At Break and/or CD Stretch At Break may be utilized in conjunction with at least one of MD Tensile Strength or CD Tensile Strength, respectively, to characterize package materials which may be sufficient to package absorbent articles as described herein. Any suitable combination of metrics may be utilized.

The package materials of the present disclosure may have an MD Tensile Strength of at least 5 kN/m, at least 7 kN/m, or at least 8 kN/m, specifically reciting all values within these ranges and any ranges formed therein or thereby. The MD Tensile Strength may be between about 5 kN/m and about 8.5 kN/m, between about 5.2 kN/m and about 8.2 kN/m, or between about 5.5 kN/m and about 8.0 kN/m, specifically reciting all values within these ranges and any ranges formed therein or thereby. The MD Tensile Strength is measured using the Strength Tensile Test Method described herein.

The package materials of the present disclosure may have a CD Tensile Strength of at least 3 kN/m, at least 4 kN/m, or at least 5.5 kN/m, specifically reciting all values within these ranges and any ranges formed therein or thereby. The CD Tensile Strength may be between about 3 kN/m and about 6.5 kN/m, between about 3 kN/m and about 6.2 kN/m, or between about 3 kN/m and about 6 kN/m, specifically reciting all values within these ranges and any ranges formed therein or thereby. The CD tensile strength is measured using the Strength Tensile Test Method.

The package materials of the present disclosure may have a Burst Strength of at least 200 kPa, at least 250 kPa, or at least 550 kPa, specifically reciting all values within these ranges and any ranges formed therein or thereby. The Burst Strength of the package materials of the present disclosure may be between about 200 kPa and about 600 kPa, between about 220 kPa and about 550 kPa, or between about 250 kPa and about 500 kPa, specifically reciting all values within these ranges and any ranges formed therein or thereby. The Burst Strength is measured using the Burst Strength Test Method described herein. It is believed that the Burst Strength, as measured, includes components of strength, flexibility, and resiliency. As such, it is believed that Burst Strength may be used independently from the other metrics mentioned.

The package materials of the present disclosure, in addition to strength, may also exhibit some measure of resiliency. Thus, the package materials of the present disclosure may exhibit an MD Stretch At Break of at least 3 percent, at least 4 percent, or at least 6 percent, specifically reciting all values within these ranges and any ranges formed therein or thereby. The package materials of the present disclosure may exhibit an MD Stretch At Break of between about 3 percent and about 6.5 percent, between about 3.2 percent and about 6.2 percent, or between about 3.5 percent and about 6 percent, specifically reciting all values within these ranges and any ranges formed therein or thereby. The MD Stretch At Break is measured using the Strength Tensile Test Method described herein.

The package materials of the present disclosure may exhibit a CD Stretch At Break of at least 4 percent, at least 6 percent, or at least 9 percent, specifically reciting all values within these ranges and any ranges formed therein or thereby. The package materials of the present disclosure may exhibit a CD Stretch At Break of from about 4 percent and about 10 percent, from about 4.5 percent and about 9.5 percent, or from about 5 percent and about 9 percent, specifically reciting all values within these ranges and any ranges formed therein or thereby. The CD Stretch At Break is measured using the Strength Tensile Test Method described herein.

Regarding Caliper, the package materials of the present disclosure may exhibit a Caliper of at least 50 μm, at least 70 μm, or at least 90 μm, specifically reciting all values within these ranges and any ranges formed therein or thereby. The package materials of the present disclosure may exhibit a Caliper of between about 50 μm and about 110 μm, from about 55 μm and about 105 μm, or from about 60 μm and about 100 μm, specifically reciting all values within these ranges and any ranges formed therein or thereby. Caliper is measured using the Caliper Test Method described herein.

Regarding Tensile Energy Absorption (TEA), the package materials of the present disclosure may exhibit an MD TEA of at least 150 $J/m^2$, greater than 170 $J/m^2$, or at least 180 $J/m^2$, specifically reciting all values within these ranges and any ranges formed therein or thereby. The package materials of the present disclosure may have an MD TEA of between about 100 $J/m^2$ and about 250 $J/m^2$, between about 125 $J/m^2$ and about 225 $J/m^2$, or between about 150 $J/m^2$ and about 200 $J/m^2$, specifically reciting all values within these ranges and any ranges formed therein or thereby.

The package materials of the present disclosure may have a CD TEA of at least 150 $J/m^2$, at least 200 $J/m^2$, or at least 250 $J/m^2$, specifically reciting all values within these ranges and any ranges formed therein or thereby. The package materials of the present disclosure may have a CD TEA of between about 150 $J/m^2$ and about 275 $J/m^2$, from about 175 $J/m^2$ and about 260 $J/m^2$, or between about 200 $J/m^2$ and about 250 $J/m^2$, specifically reciting all values within these ranges and any ranges formed therein or thereby. TEA in the MD and CD are measured according to the Strength Tensile Test Method described herein.

The Basis Weight of the package materials may affect the "feel" of the package to the consumer as well as the strength of the package. Too low of a Basis Weight and the package may feel too flimsy. Too high and the package may feel too inflexible. The package materials of the present disclosure have a Basis Weight of between about 50 gsm and about 120 gsm, between about 55 and about 115 gsm, or between about 60 gsm and about 110 gsm, specifically reciting all values within these ranges and any ranges formed therein or thereby. The Basis Weight, also referred to as "grammage", is determined according to the Basis Weight Test Method described herein.

It is worth noting that for high speed packaging processes, the lower Basis Weight of 50 gsm may provide some quality assurance outages. It is believed that high speed packaging processes may cause strain on the packaging materials that slower packaging processes may not. Therefore, where package materials are processed using a high speed manufacturing process, 60 gsm may be the lowest desirable package material Basis Weight. Where package materials are processed using a hand packing process or lower speed packaging processes, 50 gsm may be sufficient as the lowest package material Basis Weight.

The package materials of the present disclosure are different than carton board and cardboard. For example, carton board is not as flexible as the package materials of the present disclosure. Carton board is inherently stiffer than the package materials of the present disclosure and does not have the processability on high speed converting lines as does the package materials of the present disclosure. Additionally, carton board has a Basis Weight greater than 160 gsm, which is considerably higher than that of the package materials of the present disclosure.

Similarly, cardboard is also different than the package materials of the present disclosure. Cardboard has a much higher Basis Weight (greater than 200 gsm) than those of the package materials of the present disclosure. Additionally, cardboard is much less flexible than the package materials of the present disclosure. Cardboard materials are commonly fluted and comprise three plies of a paper material and, as such, are structurally different than the package materials of the present disclosure.

The package materials of the present disclosure have the advantage of being more flexible as compared to carton board and cardboard. Another advantage is that the package materials of the present disclosure take up less space than the more-bulky carton board and cardboard. A further advantage of the package materials of the present disclosure, attributable at least in part to the strength and resiliency properties discussed herein, is that the package materials allow the packaged absorbent articles to be compressed within the package. This allows for more products to fit within a smaller volume package which may increase manufacturing efficiency. One additional advantage is that a single layer (one ply) of the package materials of the present disclosure may form packages of the present disclosure. The inventors have found that, due at least in part to the flexibility, strength, and resiliency properties of the package materials, packages of the present disclosure may be formed from a single layer (one ply) of package materials of the present disclosure.

Despite having reduced flexibility compared to, for example, plastic packaging, and lower Basis Weight than cardboard and carton board, the inventors have surprisingly found the packaging materials of the present disclosure may withstand the rigors of a high speed manufacturing process—where a plurality of absorbent articles are placed within the package under compression—as well as the rigors of being shipped, provide protection from environmental insults during shipping and while on the store shelf, and provide protection for absorbent articles while in the consumers home.

Table 1 shows a variety of package materials which are able to be successfully utilized in packaging absorbent articles under high speed processing conditions, along with at least one package material which is not successful. The various properties discussed previously are also listed for each of the samples.

Sample 1: Packaging paper produced from pure, white kraft pulp and consisting entirely of virgin fibers, available from BillerudKorsnäs™ under the trade name Axello Tough White.

Sample 2: Packaging paper produced from pure, white kraft pulp and consisting entirely of virgin fibers, available from BillerudKorsnäs™ under the trade name Performance White SE.

Sample 3: Calendered specialty kraft paper consisting entirely of virgin fibers, available from Mondi™ under the trade name Advantage Smooth White Strong.

Sample 4: Packaging paper produced from kraft pulp, made of virgin fibers, and comprising a barrier coating of fluoropolymers, available from BillerudKorsnäs™ under the trade name Basix Glaze.

TABLE 1

|  | Sample 1 | Sample 2 | Sample 3 | Sample 4 |
|---|---|---|---|---|
| Basis Weight (gsm) | 80 | 70 | 70 | 50 |
| MD Tensile Strength (kN/m) | 7.6 | 5.7 | 5.9 | 4.7 |
| CD Tensile Strength (kN/m) | 4.7 | 4.1 | 3.0 | 2.7 |
| Burst Strength (kPa) | 480 | — | 256 | 185 |
| MD Stretch At Break (%) | 4.5 | 6.0 | 2.5 | — |
| CD Stretch At Break (%) | 8.0 | 9.5 | 8.0 | — |
| Caliper (μm) | 92.0 | — | 89.0 | 67.0 |
| TEA MD (J/m²) | 185 | 230 | — | — |
| TEA CD (J/m²) | 240 | 200 | — | — |

The package material of Sample 4 is not able to be successfully utilized in the packaging of absorbent articles. During the placement of absorbent article in the package, the package material tore. Without wishing to be bound by theory, it is believed that Sample 4 failed due to a combination of low Basis Weight and a high speed packaging process. While Sample 4 failed under the conditions of the high speed process, it is believed that a sample having the properties of Sample 4 may be successful with the use of a gentler packaging process, such as hand packing.

Package Configurations

The package for absorbent articles according to the present disclosure comprises a package material comprising natural fibers. The package material forms a bag 4 having a first side edge 422, a second side edge 423 opposite the first side edge, a top edge 448, and a bottom edge 420 opposite the top edge in a flat laid-out state; the first side edge 422 and second side edge 423 are substantially parallel, the top edge 448 and bottom edge 420 are substantially parallel and the first side edge 422 and second side edge 423 are substantially rectangular to the top edge 448 and bottom edge 420 in a flat laid-out state. The bag 4 with one or more absorbent articles disposed therein forms the package 1. In other words, the package 1 contains absorbent articles and its panels correspond to parts of the bag 4: the front surface 414 of the bag 4 at least partly forms the front panel 14 and the top panel 11 of the package 1; the back surface 415 of the bag 4 at least partly forms the back panel 15 and the top panel 11 of the package 1; the first side surface 412 of the bag 4 at least partly forms the first side panel 12 and may from part of the top panel 11 of the package 1; and the second side surface 413 of the bag 4 at least partly forms the second side panel 13 and may from part of the top panel 11 of the package 1. The bottom surface 410 of the bag 4 at least partly forms the bottom panel 10 of the package 1. The package material thus may also form the package 1 forming a front panel 14, a back panel 15 opposite the front panel 14, a first side panel 12, a second side panel 13 opposite the first side panel 12, a top panel 11, and a bottom panel 10 opposite the top panel 11. The panels may define an interior compartment of the package 1, and wherein one or more absorbent articles may be disposed in the interior compartment.

The package 1 is sealed along a seal line 11a such that the one or more absorbent articles are enclosed within an interior compartment of the bag 4. The seal line 11a may be present on the parts of the package 1 formed by the back surface 415, the front surface 414, the first side surface 412, and the second side surface 413 of the bag 4. The seal line 11a may be a continuous line across the parts of the package 1 formed by the front surface 414 and the back surface 415 via the first side surface 412 and the second side surface 413. The seal line 11a may be a continuous line across each of the parts of the package 1 formed by the front surface 414, the back surface 415, the first side surface 412, the second side surface 413 and may be interrupted in the edge region between the front surface 414 and first side surface 412; the edge region between the front surface 414 and second side surface 413; the edge region between the back surface 415 and the first side surface 412; and/or the edge region between the front surface 414 and second side surface 413. The seal line 11a on the front surface 414 of the bag 4 is substantially parallel to the bottom edge 420 of the bag 4 in a flat laid-out state. The seal line 411a on parts of the package 1 formed by the front surface 414 of the bag 4 may be substantially parallel to the bottom edge 420 of the bag 4 in a flat laid-out state. The seal line 11a on parts of the package 1 formed by the back surface 415 of the bag 4 may be substantially parallel to the bottom edge 420 of the bag 4 in a flat laid-out state. The seal line 11a on parts of the package 1 formed by the first side 412 and second side surface 413 of the bag 4 may be substantially parallel to the bottom edge 420 of the bag 4 in a flat laid-out state. The seal line 11a on parts of the package 1 formed by the first side 412 and second side surface 413 of the bag 4 may not be parallel to the bottom edge 420 of the bag 4 in a flat laid-out state. The seal line 11a on parts of the package 1 formed by the first side 412 and second side surface 413 of the bag 4 may have a V-shape. This may be due to the fold lines and/or gussets present in different package forms as described below.

Length $L_S$ is the distance between the seal line 411a and the top edge 448 along a direction parallel to the first side edge 422 of the bag 4 in a flat laid-out state. $L_S$ is equal to or larger than 65 mm. By choosing such a length between the seal line 411a and the top edge 448, it is ensured that the piece, which is cut off after sealing, exhibits an area sufficiently large to ensure reliable removal of the trim piece from the line, in particular via air suction means; while the package still exhibits a closing seam fin 11c after cutting. Due to the closing seam fin 11c, the distance between the trim line and the seal line is sufficiently large not to damage the seal line 11a when cutting along the trim line. Further, size and shape of the closing seam fin 11c may be chosen to facilitate gripping the package from the shelf by the consumer and to be aesthetically appealing. $L_S$ may be from 65 mm to 110 mm, preferably from 70 mm to 100 mm, more preferably from 75 mm to 95 mm. By choosing such a length, the balance between providing sufficiently large area of the trim piece to apply for removal forces while providing a sufficiently small length for the trim piece to be removed via apertures, e.g. a trim removal hole, from the line.

Length $L_B$ is the distance between the bottom edge 420 and the top edge 448 along a direction parallel to the first side edge 422 of the bag 4 in a flat laid-out state. The front surface 414 and the back surface 415 of the bag 4 may have substantially the same length $L_B$. The back surface 415 may be folded in certain configurations, which are discussed herein. The length of the back surface 415 corresponds to the distance between the bottom edge, i.e., the edge between the back surface 415 and the bottom surface 410, and the top edge, i.e., the edge between the back surface 415 and the open end 48, in a non-folded state. The first side surface 412 and the second side surface 413 of the bag 4 may have substantially the same length $L_B$. The front surface 414, the back surface 415, the first side surface 412 and the second side surface 413 of the bag 4 all may have substantially the same length $L_B$. $L_B$ may be from 150 mm to 350 mm, from 180 mm to 320 mm, or from 200 mm to 300 mm. $L_B$ may be from 150 mm to 250 mm, from 160 mm to 220 mm, or from 180 mm to 200 mm, when one stack of absorbent articles is disposed to the bag 4 to form the package 1. $L_B$ may be from 200 mm to 350 mm, from 220 mm to 320 mm, or from 250 mm to 300 mm, when two stacks of absorbent articles are disposed to the bag 4 to form the package 1. $L_S$ may be from 0.25 to 0.60, preferably from 0.30 to 0.55 times $L_B$, more preferably from 0.35 to 0.50 times $L_B$.

Length $L_P$ is the distance between the bottom edge 420 and the seal line 411a along a direction parallel to the first side edge 422 of the bag 4 in a flat laid-out state. In other words, $L_P$ corresponds to the length of the part of the front panel 14 and the top panel 11 of the package 1 formed by the front surface 414 of the bag 4. $L_B$ is the sum of $L_S$ and $L_P$. $L_P$ may be from 80 mm to 280 mm, from 110 mm to 250 mm, or from 130 mm to 230 mm. $L_P$ may be from 80 mm to 180 mm, from 90 mm to 150 mm, or from 110 mm to 130 mm, when one stack of absorbent articles is disposed in the package 1. $L_P$ may be from 130 mm to 280 mm, from 150 mm to 250 mm, or from 180 mm to 230 mm, when two stacks of absorbent articles are disposed in the package 1. $L_S$ may be from 0.50 to 1.00 times $L_P$, preferably from 0.60 to 0.95 times $L_P$, more preferably from 0.65 to 0.90 times $L_P$.

The package 1 may not comprise wicket-holes. The bag 4 may not comprise wicket-holes. The package 1 may be substantially free of holes. The bag 4 may be substantially free of holes. As trim is typically removed from the packaging line via suction means, holes, in particular wicket-holes due to their size, in the area, which is cut away from the package, may interfere with the suction means hindering the removal of trim. When trim is not removed reliably, trim pieces remaining on the line from prior packages may be enclosed in the interior compartment of the package or may even interfere with the sealing process thus causing quality issues due to contamination with trim pieces or incomplete sealing. Further, the packaging line may be blocked due to insufficient trim removal from the line or due to blockage of transporting line and/or processing equipment utilizing suction means to ensure proper placement of the pre-made bags. Further, adding wicket-holes to bags increases the complexity and production costs of pre-made bags. Typically, one the front or back surface, typically the back surface, of pre-made bags is extended and the extension comprises wicket-holes.

Alternatively, a separate piece of material comprising wicket-holes is glued to back or front surface of a bag.

All of the panels of the package 1 may comprise a unitary piece of package material. All of the surfaces of the bag 4 may comprise a unitary piece of package material. The front surface 414 and the back surface 415 of the bag 4 may be formed from a continuous package material web and are heat-sealed to one another along the first side edge 422 and second side edge 423. By this, processing on the package line can be facilitated.

The package materials of the present disclosure may be arranged as a package in a myriad of configurations to contain absorbent articles. The package comprises a plurality of panels which define an interior compartment and enclose one or more than one absorbent article. When in a sealed state, the package completely encloses the one or more than one absorbent article. Each of the panels comprises an inner surface—facing inward toward the packaged absorbent article—and an outer surface—facing outward toward the consumer. The outer surface and/or inner surface of one or more panels may comprise inks or dyes which create branding on the package, package information, and/or background color. The branding and/or package information associated with the absorbent articles within the package may be provided on an outer surface of at least one panel. Branding may include logos, trade names, trademarks, icons, and the like, associated with the absorbent articles within the package. Branding may be utilized to inform a consumer of the brand of the absorbent articles within the package. As an example, branding for a package of feminine hygiene pads may comprise the brand name Always®. Package information may include the size of the absorbent articles, the number of absorbent articles within the package, an exemplary image of the absorbent articles contained within the package, recyclability logos, and the like. As an example, package information for a package of feminine hygiene pads may comprise a size indicator, e.g., "Size 1."

The package materials of the present disclosure may be supplied by a manufacturer of package materials to an absorbent article manufacturer. The package materials may be pre-formed to some extent into a finished bag shape. Such a pre-made bag may preferably correspond to the bag 4 of the present invention. Alternatively, the manufacturer of package materials may simply provide rolls of the package materials to the absorbent article manufacturer. The package material may be unitary, meaning that a bag and package is formed from a single piece of package material. For example, multiple folds and seams may be utilized to form the plurality of panels of the package from a single piece of package material. In such examples, the absorbent article manufacturer may create the folds and seams as described herein to form a package for absorbent articles. The packages of the present disclosure may comprise package material which comprises a plurality of discrete portions. Such configurations are described in additional detail herein.

Figure 1A:
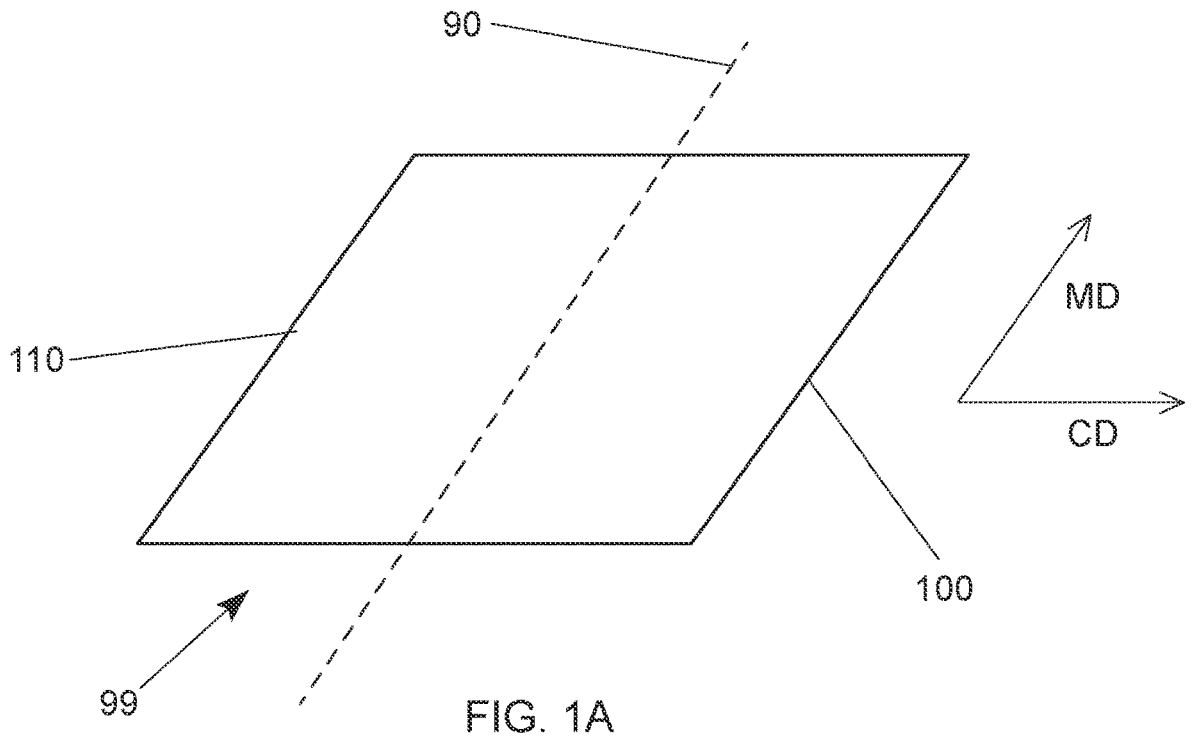
FIG. 1A is a schematic representation of a package material sheet.
Figure 1B:
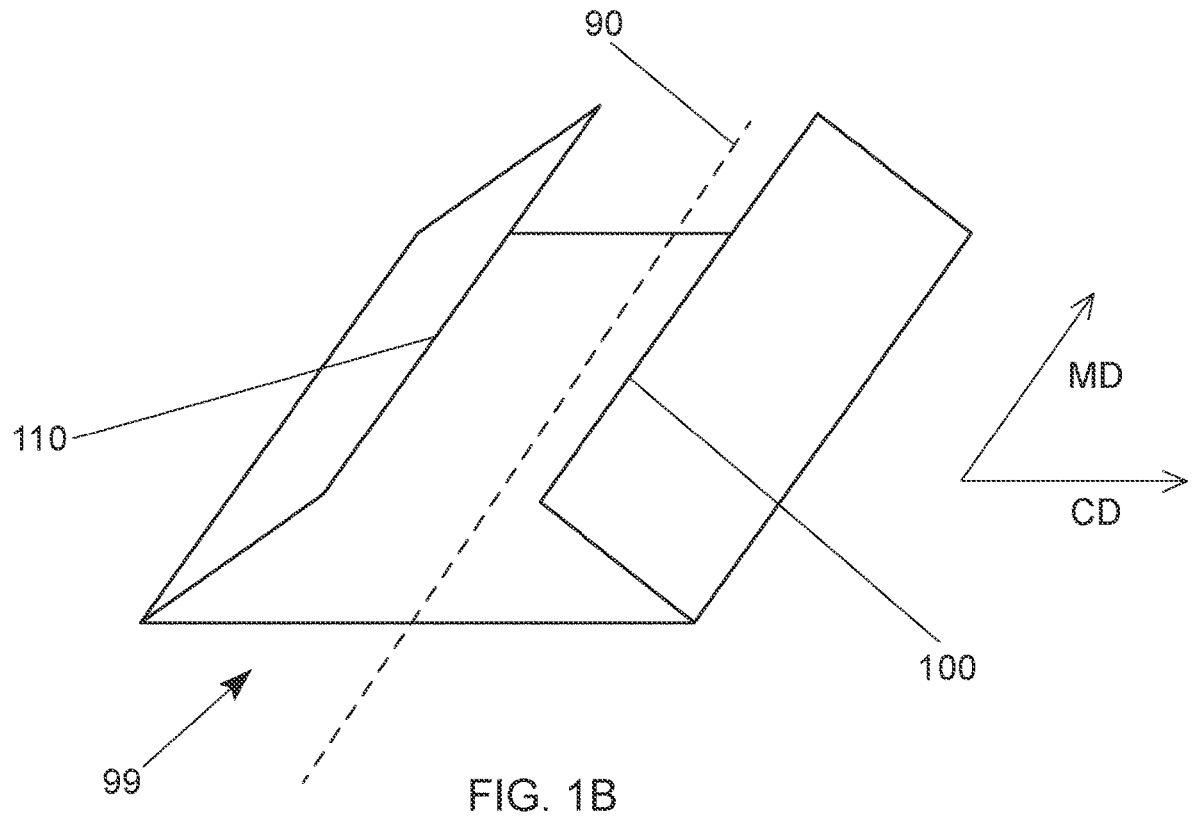
FIG. 1B is a schematic representation showing the package material sheet of FIG. 1A in a partially folded configuration.
Figure 1C:
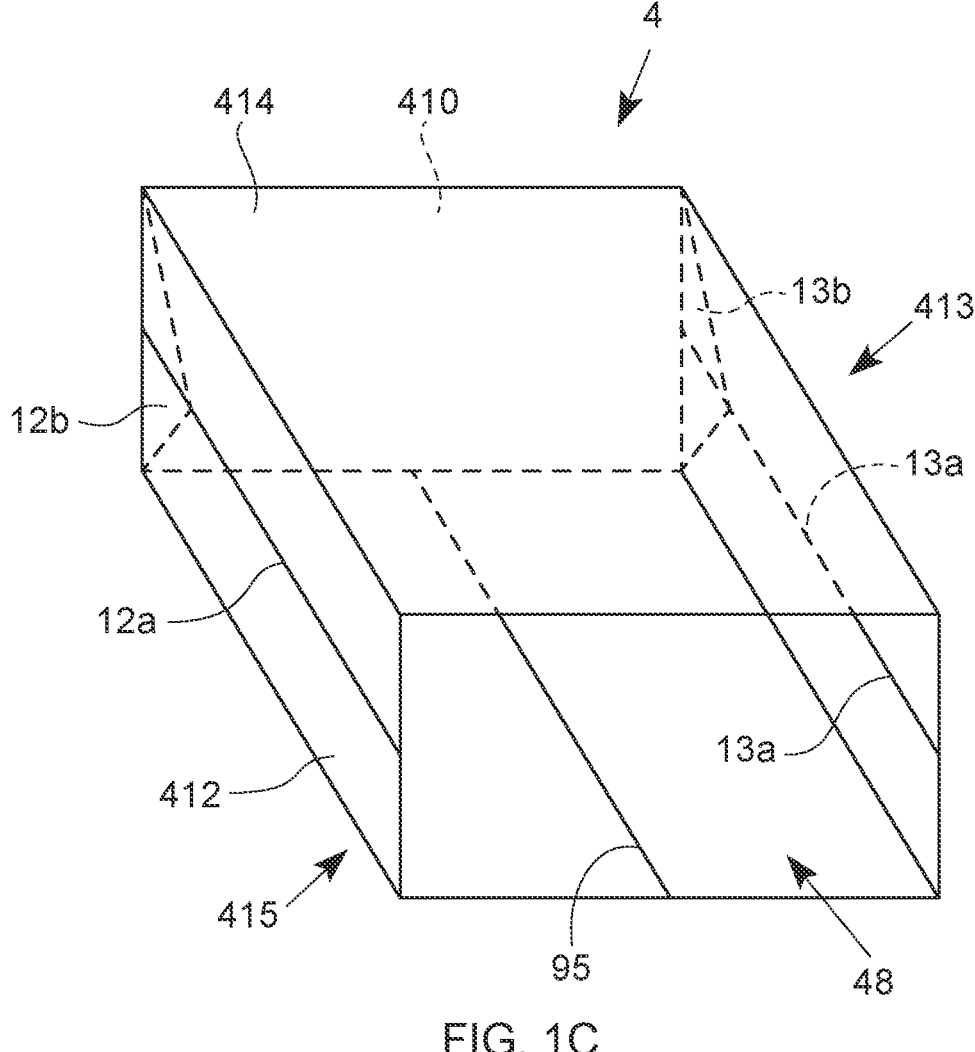
FIG. 1C is a schematic representation of a bag with an open end.

Regardless of whether the package material is on rolls or pre-formed to some extent, the packages of the present disclosure begin with paper stock. Referring to FIGS. 1A-1B, edge portions 100 and 110 of a paper stock sheet 99 may be folded towards each other and subsequently sealed to form a seam. For example, edge portions 100 and 110 of the sheet 99 may be brought inward towards a longitudinal centerline 90 of the sheet 99 to form a hoop seam 95 (see FIG. 1C). These edge portions may be overlapped with one another and sealed together to form an overlap seam. Alternatively, the edge portions 100 and 110 may be joined together on their respective inner surfaces to form a butt seam. Butt seams tend to not lay as flat as an overlap seam. Therefore, where the seam is located, at least in part, on a bottom panel upon which the package may rest, an overlap seam may be desirable such that the package may sit on a flatter bottom panel.

Figure 1D:
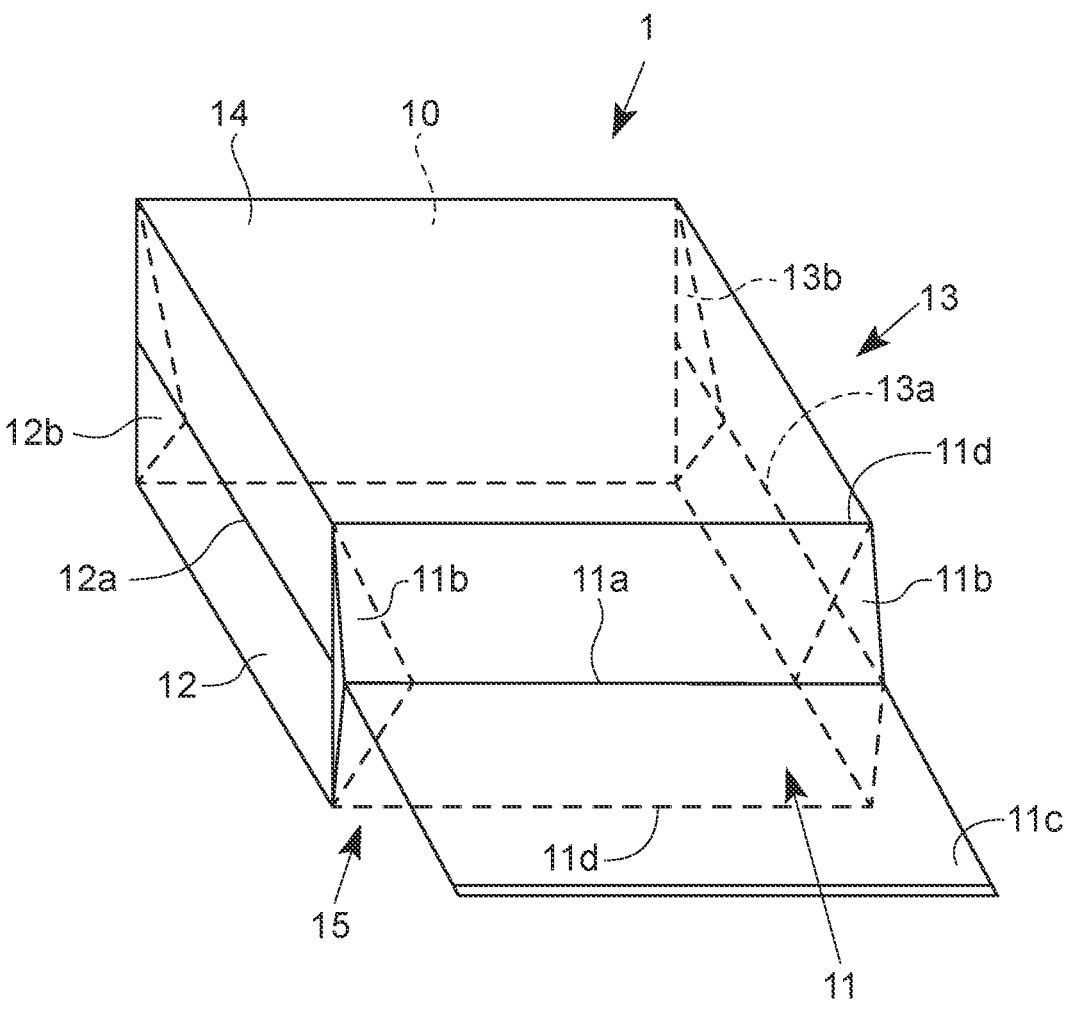
FIG. 1D is a schematic representation of the bag of FIG. 1C in a closed state forming a package; absorbent articles disposed therein are not shown.

The sheet of packaging material may be suitably folded to form bag side creases 12b and 13b and two side folds 12a and 13a on opposite sides, to form the bag structure 4 having a bottom surface 410, a first and second side surface 412, 413, respectively, and a front surface 414 and a back surface 415. An open end 48 opposes the bottom surface 410. Each side crease 12b, 13b may be located at the respective first and second side surface 412, 413. It is worth noting that in FIGS. 1C and 1D, the crease and folds shown are for a package having a block configuration or block bottom configuration. Gussets and fold lines for a pinch bottom bag are discussed in additional detail. An example is shown in FIG. 2B.

In a flat laid out state, the bag 4 has a first side edge 422 and a second side edge 423 opposite the first side edge; a top edge 448, and a bottom edge 420 opposite the top edge. The first side edge 422 and second side edge 423 are substantially parallel. The top edge 448 and bottom edge 420 are substantially parallel. The top edge 448 and bottom edge 420 are the edges with the maximal distance from the central transverse axis of the bag in a flat lait-out state. The first side edge 422 and second side edge 423 are substantially rectangular to the top edge 448 and bottom edge 420 in a flat laid-out state. The first side edge 422 and second side edge 423 are the edges with the maximal distance from the central longitudinal axis of the bag in a flat laid-out state. The top edge 448 corresponds to the edge of the front surface 414 at the open end 48 and/or the edge between of back surface 415 at the open end 48. The bottom edge 420 corresponds to the edge between the front surface 414 and bottom surface 410 and/or the edge between the back surface 415 and bottom surface 410.

In a flat laid out state, the first and second side surface 412, 413 of the bag may be folded inwards along the side creases 12b, 13b. In such a case, the first side edge 422 and the second side of the bag 4 may correspond to the edges between front surface 414 and the first and second side surface 412, 413; and/or may correspond to the edges between back surface 415 and the first and second side surface 412, 413.

The bag 4 is filled by inserting a plurality of absorbent articles, through the open end 48 to form a package 1 forming a front panel 14, a back panel 15 opposite the front panel 14, a first side panel 12, a second side panel 13 opposite the first side panel 12, a top panel 11, and a bottom panel 10 opposite the top panel 11. The panels define an interior compartment of the package, and the one or more absorbent articles are disposed in the interior compartment. When the bag 4 is filled with a plurality of articles, e.g., by loading articles from the open end 48, the device used to introduce the articles inside the bag 4 together with the articles may exert some tension on each of the first and second side surfaces 412, 413 of the bag 4, the first side panel 12 and second side panel 13 of the package 1 respectively. For example, the articles may be compressed before being inserted into the bag 4 so that the articles may slightly expand after they are introduced in the bag 4, and thus exert some tension on the first and second side surfaces 412, 413 as well as the front surface 414 and the back surface 415, the first side panel 12 and second side panel 13 as well as the front panel 14 and the back panel 15 of the package 1 respectively. The tension may be exerted on each of the creases 12b, 13b at the respective first and second side surfaces 412, 413, the first side panel 12 and second side panel 13 respectively, particularly along the first and second side folds 12a, 13a by which the package may maintain a substantially parallelepiped shape.

The open end 48 is closed via a seal to form a top panel 11. Any suitable style of closing may be utilized. In a form, top panel 11 may comprise closing gussets 11b, wherein portions of the outer surface of the package material at the closing gussets 11b are brought to form a closing seam corresponding to the seal line 11a and a closing seam fin 11c extending from the closing seam, and top panel 11. At least a portion of the closing seam fin 11c may be attached to at least a portion of the top panel 11. Tacking down the closing seam fin 11c to at least a portion of top panel 11 may reduce the risk of unintentional opening of the package, provide for increased stackability, as well provide a cleaner look on-shelf look. Instead of forming closing gussets and a closing fin, top panel 11 may comprise seams which are joined together in a block style configuration or cross style configuration, discussed further herein.

An example of a block style configuration is shown in FIG. 2A. The bottom surface of the back 410 may comprise block style seams 220 and 230. The bottom surface 410 may comprise a base portion 240. A first flap of package material 250 may be folded onto the base portion 240. First seams 220 may be provided to attach the first flap of package material 250 to the base portion 240. A second flap of package material 260 may be folded onto the base portion 240 and on top of the first flap of package material 250. Second seams 230 may be provided to attach the second flap of package material 260 to the base portion 240 and to the first flap of package material 250.

Another example of a sealing style which may be utilized with the packages of the present disclosure is the pinch style configuration or the pinch bottom style. An example of a pinch style configuration is shown in FIG. 2B. As shown, one of the key differences between the block bottom and the pinch bottom configuration is the configuration of the creases 12b and 13b. Instead of creases on the sides 412 and 413, a pinch style configuration comprises gussets 22b and 23b on the bottom surface 410. Additionally, in the pinch bottom configuration, the bottom surface 410 comprises a fold line 10a which may be absent in the block style configuration.

Cross style or cross bottom style configurations are also acceptable for sealing portions of the package materials of the present disclosure. An example of a cross style configuration is shown in FIG. 2C. As shown, one of the key differences between the cross style configuration and the block style configuration is that gussets 32b and 33b and fold lines 12a and 13a are oriented outward of the interior of the bag 4 prior to filling bag 4 to form the package 1. In a block-style configuration (FIG. 1C), on the other hand, fold lines 12a and 13a on the first side surface 412 and the second side surface 413, respectively, are oriented inward prior to filling bag 4 to form the package 1. Due to the orientation of the gussets 32b and 33b in the cross style configuration, filling the bag 4 with absorbent articles may require less energy to expand the bag 4 for filling. As an example, creases oriented inward, e.g., block style configuration, would require displacement outward of the creases prior to filling the bag to form the package. Additionally, the equipment utilized in guiding the product into the bag 4 may have a reduced likelihood of interfering with the gussets, given their orientation outward. This may reduce the likelihood of packaging mishaps or manufacturing process stoppages due to quality issues.

Similar to the block style configuration, the bottom surface 410 of the cross style configuration comprises seams 320 and 330. The bottom surface 410 comprises a base portion 340. A first flap of package material 350 may be folded onto the base portion 340. First seams 320 may be provided to attach the first flap of package material 350 to the base portion 340. A second flap of package material 360 may be folded onto the base portion 340 and on top of the first flap of package material 350. Second seams 330 may be provided to attach the second flap of package material 360 to the base portion 340 and/or to the first flap of package material 350. A similar execution may be utilized to form the closure on the sixth surface (formed once the package is sealed after the placement of absorbent articles therein).

For less bulky items, where standability of the package is desired, the block bottom or cross bottom may be desirable, as these configurations form a flat base. However, for bulky items, the pinch style configuration bags may be beneficial as the bulky absorbent articles therein may form a steady base for the package to stand. The inventors have surprisingly found that diapers may be suited for pinch bottom bags due their bulky nature. In contrast, feminine hygiene articles, particularly menstrual pads, may be suited for block bottom configured packages.

Additionally, it is worth noting that block style and cross style configured packages tend to be themselves bulkier than their pinch style counterparts. For the purposes of packaging absorbent articles, unfilled packages may arrive pre-formed in stacks to an absorbent article manufacturer. Typically, stacks of pre-formed block style and cross style configuration packages will take up more space—due to their bulkiness—as compared to pre-formed pinch style packages. The bulkiness of the block and cross style configurations may make the stacks more difficult to manipulate during the filling process, particularly where a large number of filled packages are created per minute. In such instances, the bulkiness of these configurations may mean an increased frequency of replenishment of the stacks.

Referring back to FIGS. 1C-ID, the bottom surface 410 of the bag 4 may form at least a portion of the bottom panel 10 of the package 1. It is worth noting that if the bottom panel 10 comprises seams, the seams may be hidden from view on the store shelf. The first and second side surfaces 412 and 413, as they may comprise side creases 12b and 13b, respectively, may form at least a portion of the first side panel 12 and the opposite second side panel 13, respectively, or vice versa. The front and back surfaces 414, 415 may form at least a portion of the front panel 14 and an opposite back panel 15, respectively, or vice versa. At least one of the front and back surfaces 414, 415 may comprise branding, product information and/or background color as described herein, as the front panel 14 is generally the consumer-facing panel. However, product information and/or background color may not be limited to the consumer-facing panel. Any combination of the panels of the packages of the present disclosure may comprise branding, product information, and/or background color. The top panel 11 may comprise closing gussets 11b, closing scam 11a, and a closing seam fin 11c extending from the closing seam 11a. In this way the closing gussets 11b and closing seam fin 11c do not introduce bulk and instability to the base of the package. A top edge region 11d is formed at the transition from the top panel to the front, back, and first and second side panels. The top edge region 11d may be formed by portions of the top, front, back, first side, and second side panels that are adjacent to a fold in the package material designating a transition from the top panel to another panel.
Absorbent Article Configuration The packages of the present disclosure comprise one or more absorbent articles. The absorbent articles may be placed into the package in an unfolded or folded configuration. The articles may be folded laterally and/or longitudinally. The articles may comprise one fold line, and may be disposed within the package in a bi-fold configuration. The articles may comprise two fold lines, and may be disposed within the package in a tri-fold configuration.

Figures 3A, 3B:
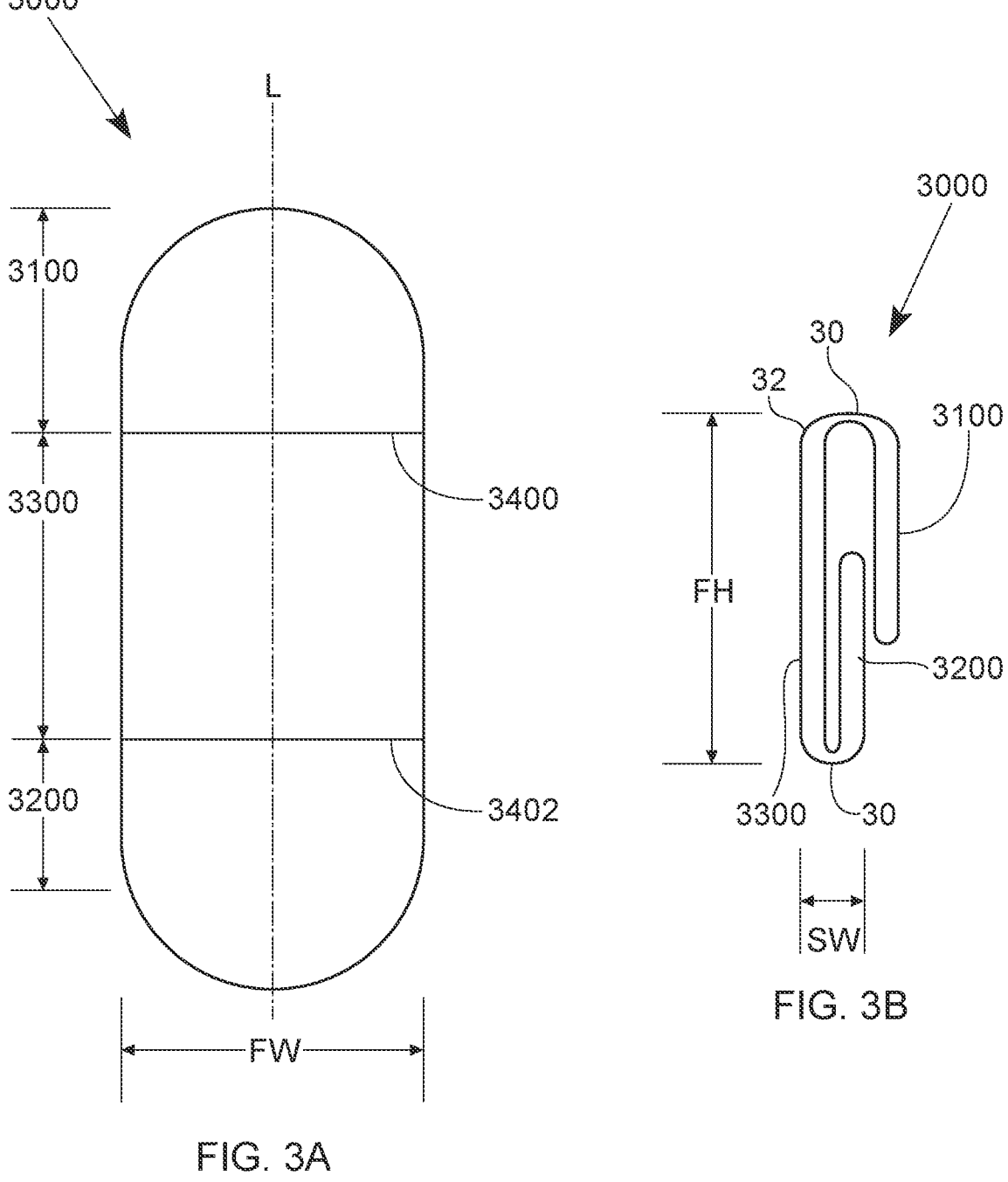
FIG. 3A is a plan view of an example of an absorbent article in the form of a feminine hygiene pad in an unfolded configuration.
FIG. 3B is an edge side view of the feminine hygiene pad of FIG. 3A, shown folded about lateral fold lines in a tri-fold configuration.

FIG. 3A depicts an example of a feminine hygiene pad in an unfolded configuration. FIG. 3B depicts a side view of the feminine hygiene pad of FIG. 3A in a tri-fold configuration. The feminine hygiene pad depicted in FIGS. 3A and 3B comprises a first fold line 3400 disposed between a first end region of the pad 3100 and a central region of the pad 3300, and a second fold line 3402 disposed between a second end region of the pad 3200 and the central region 3300. Prior to placement within the package, the second end region 3200 may be folded over and longitudinally inward about the second fold line 3402 to overlap at least a portion of the central region 3300, as may be appreciated from a comparison of FIGS. 3A and 3B. The first end region 3100 may then be folded over and longitudinally inward about the first fold line 3400 to overlap at least a portion of the central region 3300 and a portion of the second end region 3200. In some examples a tri-fold configuration may have the article folded approximately in thirds, about the two longitudinally-spaced lateral fold lines.

Figure 4A:
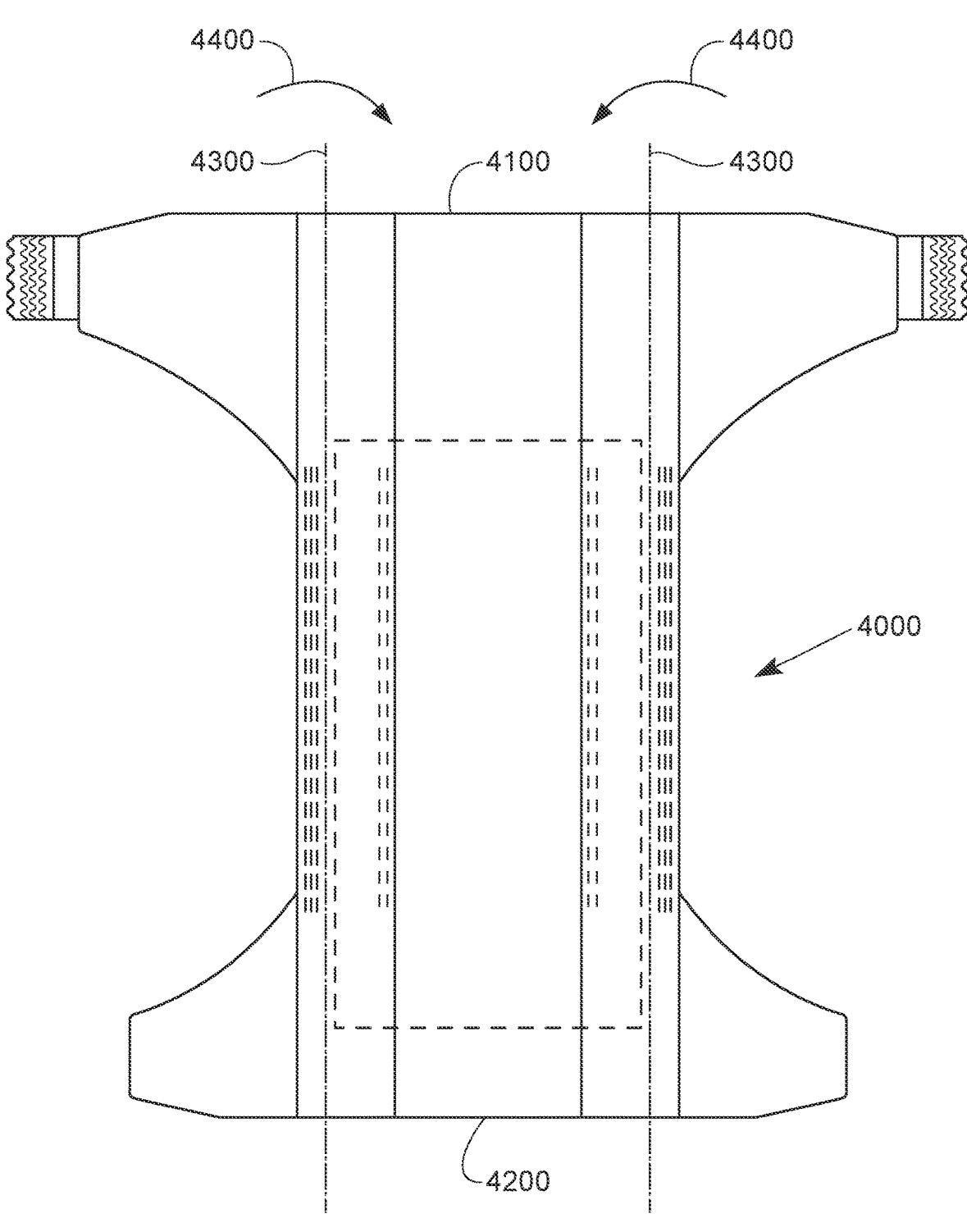
FIG. 4A is a plan view of an example of an absorbent article in the form of a disposable diaper, wearer-facing surfaces facing the viewer.
Figure 4B:
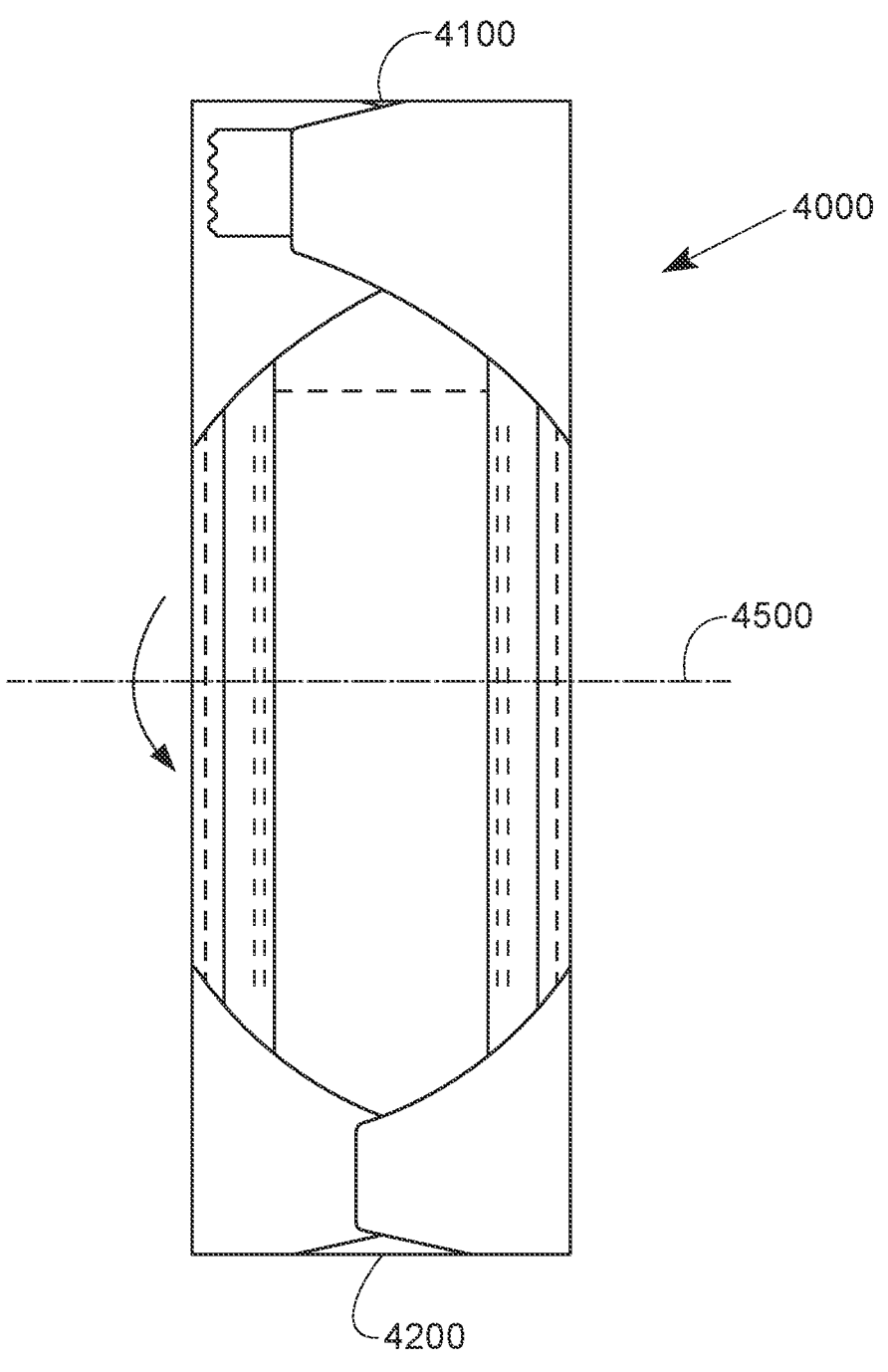
FIG. 4B is a plan view of the diaper of FIG. 4A, shown with side portions folded over and laterally inward about longitudinal side edge fold lines.

FIGS. 4A-4D depict an absorbent article in the form of a diaper 4000 with front and rear waist edges 4100, 4200, in successively open/unfolded and folded configurations. For packaging in bulk, each of a plurality of diapers such as that shown in FIG. 4A may, in a possible first step, have its longitudinal side portions be folded over and laterally inward about longitudinal side edge fold lines 4300, represented by arrow 4400, as may be appreciated from a comparison of FIGS. 4A and 4B. Next, the diaper may, in a second step, be folded longitudinally, about lateral fold line 4500 that passes through the crotch region of the diaper, as may be appreciated from a comparison of FIGS. 4B and 4C. For a bi-fold configuration such as depicted in FIGS. 4C and 4D, the article may be folded longitudinally once, and may in some examples be folded approximately in half about the lateral fold line 4400.

Regardless of whether the article is in a bi-fold or tri-fold configuration, the folded article, such as folded feminine hygiene pad 3000 and/or folded diaper 4000, may have a single fold nose 30 defining at least one end edge of the folded article, fold nose corners 32, and left and right longitudinal peripheral edges 4600, 4700. It will be appreciated that in a tri-fold example, a single fold nose may define each of both end edges of the folded article. In some examples, such as depicted in FIGS. 4C and 4D, fold nose 30 may be proximate the crotch region of the article (the middle region of the article adapted to be located between the wearer's legs during wear). The folded article will have a folded width FW measured as the distance between side edges, a folded height FH measured as the distance between fold nose 30 and the end edges (in the case of a bi-fold configuration) or between the two fold noses 30 (in the case of a tri-fold configuration), and a side width (SW). The folded width (FW) forms the flat, broad face of the folded absorbent article, while the side width (SW) forms the narrow folded side of the absorbent article.

Figure 5A:
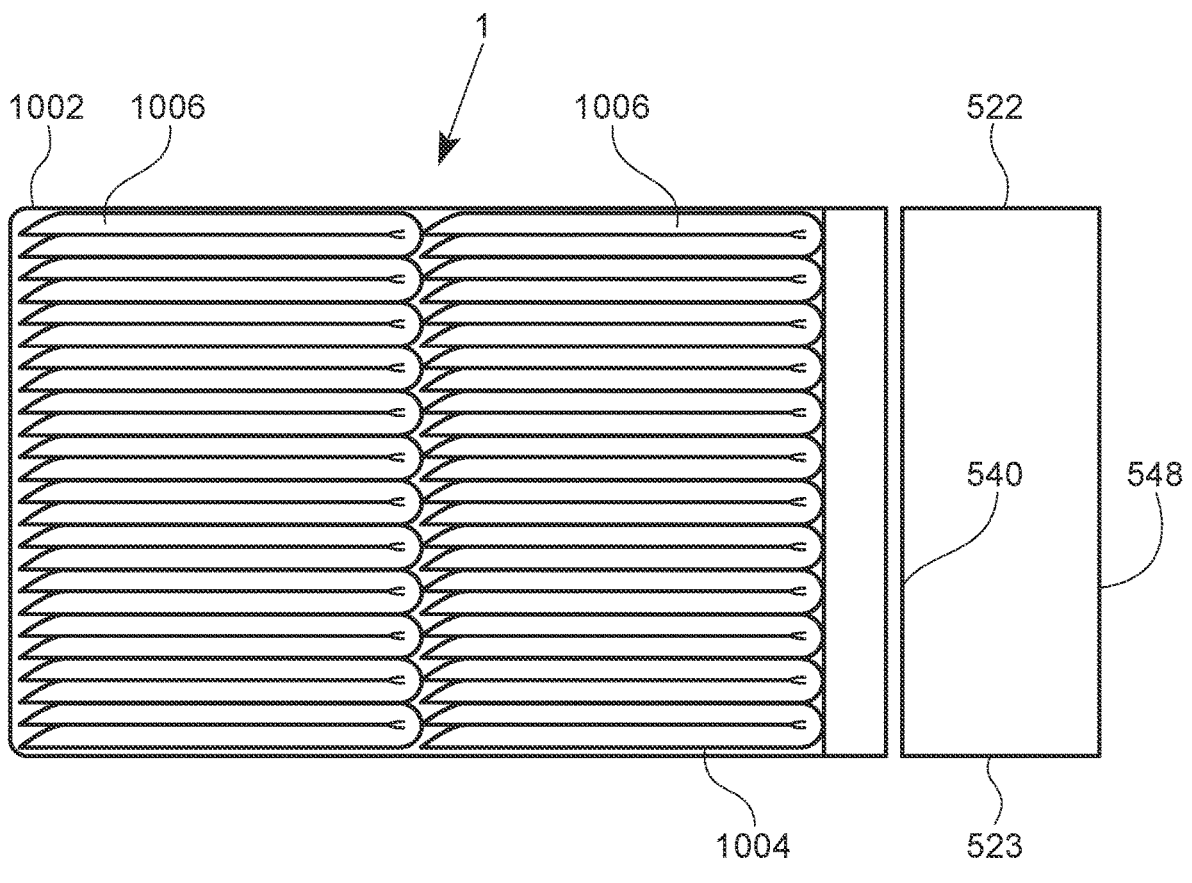
FIG. 5A is a front view of a set comprising a package, within which of a plurality of absorbent articles is disposed, and a trim piece.
Figure 5B:
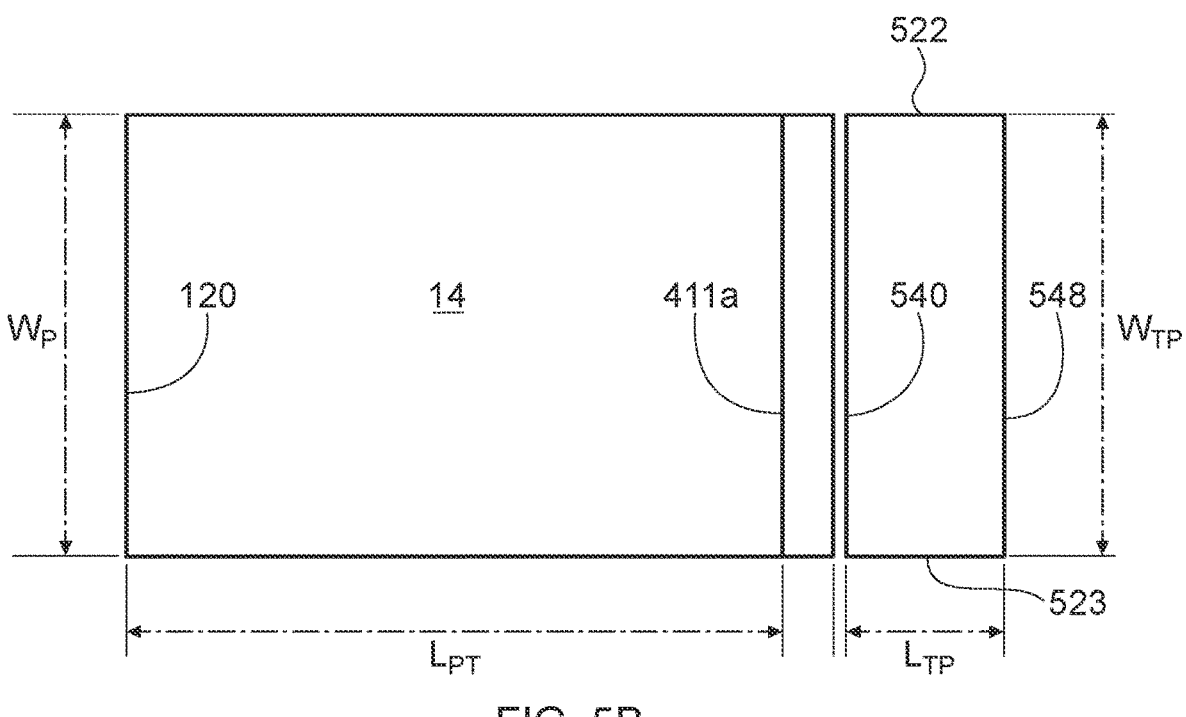
FIG. 5B is a plan view of a set comprising a package in an empty flat laid-out state and a trim piece flat laid-out state.

A plurality of folded articles such as depicted in FIGS. 3B and 4C and 4D may be placed in similar orientation within the interior compartment of a package of the present disclosure. FIG. 5A depicts a plurality of absorbent articles disposed within a package of the present disclosure. As shown in FIG. 5A, the package 1 defines an interior compartment 1002 in which a plurality of absorbent articles 1004 are situated. The plurality of absorbent articles 1004 may be arranged in a single horizontal row, or in one or more vertical stacks 1006. This is exemplarily shown in FIG. 5A. Where the articles are arranged in more than one vertical stack, all the articles may be oriented in the same direction. In another example, a first set of the plurality of folded articles may have their fold noses 30 oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack.

The folded absorbent articles may be disposed within the package of the present disclosure such that the folded width (FW) faces toward the first and second side panels. Such a configuration may be employed where the number of absorbent articles within the package is relatively large, e.g., greater than about ten individual absorbent articles, because the narrower sides (SW) of the articles will form front and back panels. Therefore, a relatively large number of absorbent articles may then be utilized to build up the front and back panels of the package. Such a configuration may be beneficial where the front and/or back panels form the consumer-facing panel.

The folded absorbent articles may be disposed within the package of the present disclosure such that the folded width (FW) faces toward the front and back panels. Such a configuration may be employed where the number of absorbent articles within the package is relatively low, e.g., less than about ten individual absorbent articles, because the wider sides (FW) of the articles will form front and back panels. Such a configuration may be beneficial where the front and/or back panels form the consumer-facing panel, and the number of absorbent articles disposed within the package is less than about ten.

The absorbent articles or articles may be packed under compression so as to reduce the size of the package, while still providing an adequate number of absorbent articles per package. By packaging the absorbent articles under compression, caregivers can easily handle and store the packages, while also providing distribution savings to manufacturers owing to the reduced size of the packages. Despite lacking the stretch properties of conventional plastic packaging material, the inventors have surprisingly found the package materials of the present disclosure are able to withstand the processing and distribution rigors, as mentioned herein, even with absorbent articles which are compressed within the package and without the use of an intermediate container. This is particularly unexpected as the materials of the present disclosure may not display the stretch properties of presently used conventional plastic films.

Packages of absorbent articles of the present disclosure may have an In-Bag Stack Height of less than about 150 mm, less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 150 mm, from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test Method described herein.

Process for Forming a Package for Absorbent Articles

A process for forming a package for absorbent articles is also disclosed. The process comprises the steps of:

a) A package material comprising natural fibers forming a bag 4 is provided. The bag 4 has a first side edge 422, a second side edge 423 opposite the first side edge 422, a top edge 448, and a bottom edge 420 opposite the top edge 448 in a flat laid-out state. The first side edge 422 and second side edge 423 are substantially parallel. The top edge 448 and bottom edge 420 are substantially parallel and the first side edge 422 and second side 423 edge are substantially rectangular to the top edge 448 and bottom edge 420 in a flat laid-out state. The bag 4 has an inside facing surface and an outside facing surface, wherein the inside facing surface comprises a scalable material. Preferably, the scalable material may comprise polyethylene. Alternatively, the sealable material may be an adhesive as described herein, or a combination of a polyethylene based material and an adhesive. The bag may have a front surface 414 and a back surface 415 and the front surface 414 and the back surface 415 have substantially the same length $L_B$. This may only apply when the front surface 414 and the back surface 415 are not folded. The bag may have a first side surface 412 and a second side surface 413 and the first side surface 412 and the second side surface 413 have substantially the same length $L_B$.

The package material may be provided as a pre-made bag. The package material may be provided in stacks of bags 4. The stacks of bags may be provided without utilizing wicket pins. In particular, the bags 4 provided may not comprise wicket-holes. The bags 4 may be free of holes, except for the open end 48. The stacks of bags may be provided to a supply equipment, in particular a cassette-like magazine, ensuring a continuous bag supply to the packaging line. The bags 4 may be oriented horizontally in the supply chamber. Each bag 4 may be separately fed to the packaging line. In particular, each bag 4 may be individually placed on a transporting line. The bags 4 may be retained to the transporting line via air suction means. Holes, particularly wicket-holes due to their relatively large size, may disturb the interaction between the bag and the air suction means leading to decreased adherence forces between the transporting line and the bags 4.

b) Disposing one or more absorbent articles through an open end 48 located at the top edge 448 to the bag 4 to form a package 1 with an interior compartment defined by a front panel 14, a back panel 15 opposite the front panel 14, a first side panel 12, a second side panel 13 opposite the first side panel 12, a top panel 11, and a bottom panel 10 opposite the top panel 11 formed by the package material.

To create an open end 48 sufficiently large to place one or more stacks of two or more absorbent articles the front surface 414 of the bag 4 has to be lifted. A stack may comprise 2 to 30, preferably 5 to 25, more preferably 8 to 20, or even 10 to 15, absorbent articles. Preferably, 1 to 5 stacks or 1 to 3 stacks of absorbent articles may be disposed. The top surface 414 of the bag 4 may be lifted to create the open end 48 utilizing suction means, in particular air suction, while the back surface 415 is held to the transporting line via air suction means. Through the created open end 48, a mechanical spreader may be introduced prior to disposing the absorbent articles.

c) Scaling the package along a seal line 11a such that the one or more absorbent articles are enclosed within the interior compartment. The seal line 411a on a front surface 414 of the bag 4 is substantially parallel to the bottom edge 420 of the bag 4 in a flat laid-out state. Length $L_S$ is the distance between the seal line and the top edge 448 along a direction parallel to the first side edge 422 of the bag in a flat laid-out state. $L_S$ is equal to or larger than 65 mm.

d) Cutting the package along a trim line, which is located between the seal line and the top edge 448 and is substantially parallel to the seal line. For steps c) and d), the front surface 414 and the back surface 415 forming at least part of the front 14 and part of top panel 11, at least part of the back 15 panel and part of the top panel 11 respectively, may be brought into contact and pressure applied from the top and/or the bottom. Then the package 1 may be sealed and then cut. Alternatively, the package 1 may be cut and then sealed. In a further alternative, the package may be sealed and cut in parallel. In particular, the unsealed package may be pressed to a cut surface. The cut surface may have a cut slid along which the package may be cut. The cut slid may be substantially parallel to the seal line 11a of the package 1. The cut surface may further comprise a trim removal hole through which the trim piece may be removed from the line via air suction means. The trim removal hole may have an obround shape, a rectangular shape or a curved-edge rectangular shape. The trim removal hole has a maximum width $W_{RH}$. $W_{RH}$ may be from 0.70 to 1.00 times, preferably 0.80 to 1.00 times, more preferably 0.85 to 0.95 times or even 0.90 to 0.93 times the width $W_{TP}$ of the trim piece. The maximum width $W_{RH}$ may be parallel to the package width $W_P$, when the package is pressed onto the cut surface. The maximum width $W_{RH}$ may preferably be parallel to cut slid. The maximum width $W_{RH}$ may be smaller than the width of the cut slid. The cut surface may comprise placements holes, which may be smaller than the trim removal hole. The placements holes may have a diameter of from 2.0 mm to 10.0 mm, preferably from 3.0 mm to 8.0 mm or from 4.0 mm to 6.0 mm. The cut surface may comprise from 50 to 300, preferably from 100 to 250 placements holes. The placements holes may be arranged in one or more rows, preferably in 2 to 8 rows, more preferably 4 to 6 rows, parallel to the cut slid. One or more rows, preferably in 2 to 5 rows, more preferably 3 to 4 rows, of placement holes may be at least partially located between the cut slid and the trim removal hole. The package 1, in particular the parts of the package 1 formed by the back surface 415 of the bag 4, may be held to the cut surface via air suction means through the placements holes before and after cutting. The trim piece may be held to the cut surface via air suction means through the placements holes after cutting. By this, the unsealed package 1 may be properly placed on the cut surface and the trim piece may be held in place before removing it from the line.

e) Removing the trim piece corresponding to the cut part. In particular, the trim may be removed via air suction means. $L_T$ is the distance between the top edge (448) and the trim line along a direction parallel to the first side edge (422) of the bag in a flat laid-out state. $L_T$ may be equal to or larger than 0.80 times $L_S$. In particular, $L_T$ may be from 0.80 to 1.00, preferably from 0.83 to 0.98 times $L_S$, more preferably from 0.85 to 0.95 times $L_S$, even more preferably from 0.88 to 0.93 times $L_S$, or even from 0.90 to 0.92 times $L_S$. $L_T$ may be equal to or larger than 55 mm, preferably equal to or larger than 58 mm, more preferably equal to or larger than 60 mm, even more preferably equal to or larger than 65 mm, or even equal to or larger than 70 mm. $L_T$ may be equal to or less than 120 mm, preferably equal to or less than 110 mm, more preferably equal to or less than 100 mm, even more preferably equal to or less than 90 mm, or even equal to or less than 80 mm. By balancing the size of the trim piece, removal of the trim from the line is facilitated. In particular, choosing a smaller size may lead to the trim remaining at the line and thus potentially interfering with line operation, e.g., by blocking the removing means. Further, the trim may interfere with the sealing process. A balanced size is particular important, when the trim is removed via air suction means.

Set Comprising a Package for Absorbent Articles and a Trim Piece

A set comprising a trimmed package for absorbent articles and a trim piece is also provided. The trimmed package comprises a package material comprising natural fibers. The trim piece comprises a trim material which is identical to the package material. The package material forms a front panel 14, a back panel 15 opposite the front panel 14, a first side panel 12, a second side panel 13 opposite the first side panel 12, a top panel 11, and a bottom panel 10 opposite the top panel 10. The panels define an interior compartment of the trimmed package. One or more absorbent articles are disposed in the interior compartment. The trimmed package is sealed along a seal line 411*a* such that the one or more absorbent articles are enclosed within the interior compartment. The seal line 411*a* substantially parallel to the bottom edge 120, which is the edge between the front panel 14 and the bottom panel 10, of the trimmed package. The trim material forms a trim piece having a first side edge 522, a second side edge 523 opposite the first side edge 522, a top edge 548, and a bottom edge 540 opposite the top edge 548 in a flat laid-out state; the first side edge 522 and second side edge 523 are substantially parallel, the top edge 548 and bottom edge 540 are substantially parallel and the first side edge 522 and second side edge 523 are substantially rectangular to the top edge 548 and bottom edge 540 in a flat laid-out state. the trim material piece has openings on the top 548 and bottom edge 540. $L_{TP}$ is the distance between the top edge 548 and the bottom edge 540 along a direction parallel to the first side edge 522 of the trim material piece in a flat laid-out state. $L_{TP}$ may correspond to $L_T$. $L_{TP}$ is equal to or larger than 55 mm. $L_{TP}$ may be equal to or larger than 55 mm, preferably equal to or larger than 58 mm, more preferably equal to or larger than 60 mm, even more preferably equal to or larger than 65 mm, or even equal to or larger than 70 mm. $L_{TP}$ may be equal to or less than 120 mm, preferably equal to or less than 110 mm, more preferably equal to or less than 100 mm, even more preferably equal to or less than 90 mm, or even equal to or less than 80 mm. $L_{PT}$ is the distance between the bottom edge 120 and the seal line 11*a* along a direction parallel to the first side edge between the first side panel 13 and the front panel 14 of the trimmed package in an empty flat laid-out state. $L_{PT}$ may correspond to $L_P$. $L_{TP}$ may be equal to or larger than 0.40 times $L_{PT}$.

The set may be formed by cutting the package for absorbent articles 1 as described herein along a trim line between the seal line and the top edge 448 of the bag 4. The set may be formed via the process for forming a package for absorbent articles described herein.

The trim piece has a width $W_{TP}$, which is the distance from the first side edge 522 to the second side edge 523 in a flat laid-out state. The trimmed package has a width $W_P$, which is the distance from the first side edge between the front panel 14 and the first side panel 12 to the second side edge between the front panel 14 and the second side panel 13. $W_{TP}$ may be equal to $W_P$.

Test Methods

Strength Tensile Test Method

The Strength Tensile Test Method is run according to ASTM D828-16 "Standard Test Method for Tensile Properties of Paper and Paperboard Using Constant-Rate-of-Elongation Apparatus" with the following specifications and/or modifications: Two sets of test specimens are cut from package materials containing a weakened region. The first set of test specimens contain the weakened region, such that the weakened region is disposed the entire way across the width test sample and is centered along and perpendicular to the length of the test specimen. The second set of test specimens are cut from the same package materials and are oriented in the same direction as the first set but do not include a weakened region. The specimen length is about 101.6 mm (4 in.) to allow sufficient specimen for clamping in the instrument grips with a distance between the grips of 50.8 mm (2 in.). The rate of grip separation during the test is 300 mm/min. When placing the test specimens containing the weakened region into the grips for testing, the path of the weakened region is to be centered between the grips and perpendicular to the pull axis of the tensile tester. The average tensile strength of the first specimen set containing the weakened region is reported as the Weakened Region Tensile Strength (WRTS) to the nearest 0.01 kN/m. The average tensile strength of the second specimen set without the weakened region is reported as the Package Tensile Strength (MD or CD) to the nearest 0.01 kN/m.

Burst Strength Test Method

Burst strength is the maximum uniformly distributed pressure that a test sample can withstand. Burst strength is measured in accordance with compendial method ISO 2758 using a test apparatus as described within the method. A suitable instrument is the 13-60 Burst Tester for Paper and Foils available from Testing Machines, Inc (New Castle, DE), or equivalent. The instrument is calibrated and operated as per the manufacturer's instructions. All measurements are performed in a laboratory maintained at 23° C.±/-2° C. and 50%±/-2% relative humidity, and test samples are conditioned in this environment for at least 2 hours prior to testing.

Measurements are made on test samples taken from rolls or sheets of the raw material, or test specimens obtained from a finished package. When excising a test sample from a finished package, use care to not impart any contamination or distortion to the test sample during the process. The test sample must be larger than the clamps used to hold the test sample in the instrument. The test sample should be taken from an area free of folds, wrinkles, or seams.

Measure the burst strength (using a clamping pressure sufficient to prevent slippage during the test, and a pumping rate of 95±15 mL/min) for a total of 10 replicate test samples. For samples that are sided, the side of the test sample that is meant to face the inside of the package faces the pressure when placed into the clamps, and 10 replicates are tested in this orientation. For samples that are balanced (not sided), 5 replicates are tested with the inside of the package facing the pressure and 5 replicates are tested with the outside of the package facing the pressure, and the results are averaged together. Record the pressure at which each test sample bursts to the nearest 0.001 kPa. If the burst pressure is less than 70 kPa, multiple layers of the test material must be used. To obtain the burst strength, divide the burst pressure by the number of layers tested. Calculate the arithmetic mean burst pressure for all replicates and report as Burst Strength to the nearest 0.001 kPa.

Caliper Test Method

The caliper, or thickness, of a single-layer test sample is measured under a static load by a micrometer, in accordance with compendial method ISO 534, with modifications noted herein. All measurements are performed in a laboratory maintained at 23° C.±2° C. and 50%±2% relative humidity and test samples are conditioned in this environment for at least 2 hours prior to testing.

Caliper is measured with a micrometer equipped with a pressure foot capable of exerting a steady pressure of 70 kPa±0.05 kPa onto the test sample. The micrometer is a dead-weight type instrument with readings accurate to 0.1 micron. A suitable instrument is the TMI Digital Micrometer Model 49-56, available from Testing Machines Inc., New Castle, DE, or equivalent. The pressure foot is a flat ground circular movable face with a diameter that is smaller than the test specimen and capable of exerting the required pressure. A suitable pressure foot has a diameter of 16.0 mm. The test sample is supported by a horizontal flat reference platform that is larger than and parallel to the surface of the pressure foot. The system is calibrated and operated per the manufacturer's instructions.

Measurements are made on single-layer test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample is ideally 200 mm$^2$ and must be larger than the pressure foot.

To measure caliper, first zero the micrometer against the horizontal flat reference platform. Place the test sample on the platform with the test location centered below the pressure foot. Gently lower the pressure foot with a descent rate of 3.0 mm per second until the full pressure is exerted onto the test sample. Wait 5 seconds and then record the caliper of the test sample to the nearest 0.1 micron. In like fashion, repeat for a total of ten replicate test samples. Calculate the arithmetic mean for all caliper measurements and report the value as Caliper to the nearest 0.1 micron.

Basis Weight Test Method

The basis weight of a test sample is the mass (in grams) per unit area (in square meters) of a single layer of material and is measured in accordance with compendial method ISO 536. The mass of the test sample is cut to a known area, and the mass of the sample is determined using an analytical balance accurate to 0.0001 grams. All measurements are performed in a laboratory maintained at 23° C.±2° C. and 50%±2% relative humidity and test samples are conditioned in this environment for at least 2 hours prior to testing.

Measurements are made on test samples taken from rolls or sheets of the raw material, or test samples obtained from a finished package. When excising the test sample from a finished package, use care to not impart any contamination or distortion to the sample during the process. The excised sample should be free from residual adhesive and taken from an area of the package that is free from any seams or folds. The test sample must be as large as possible so that any inherent material variability is accounted for.

Measure the dimensions of the single layer test sample using a calibrated steel metal ruler traceable to NIST, or equivalent. Calculate the Area of the test sample and record to the nearest 0.0001 square meter. Use an analytical balance to obtain the Mass of the test sample and record to the nearest 0.0001 gram. Calculate Basis Weight by dividing Mass (in grams) by Area (in square meters) and record to the nearest 0.01 grams per square meter (gsm). In like fashion, repeat for a total of ten replicate test samples. Calculate the arithmetic mean for Basis Weight and report to the nearest 0.01 grams/square meter.

In-Bag Stack Height Test Method

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e., each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised, and an absorbent article package is placed centrally under the horizontal sliding plate in such a way that the absorbent articles within the package are in a horizontal orientation (see FIG. 5A). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured, and the arithmetic mean is reported as the package width. The "In-Bag Stack Height"=(package width/absorbent article count per stack)×10 is calculated and reported to within ±0.5 mm.

Contemplated Examples

Example AA: A package for absorbent articles comprising: a package material comprising natural fibers; wherein the package material forms a bag (4) having a first side edge (422), a second side edge (423) opposite the first side edge, a top edge (448), and a bottom edge (420) opposite the top edge in a flat laid-out state; the first side edge (422) and second side edge (423) are substantially parallel, the top edge (448) and bottom edge (420) are substantially parallel and the first side edge (422) and second side edge (423) are substantially rectangular to the top edge (448) and bottom edge (420) in a flat laid-out state; wherein the bag (4) with one or more absorbent articles disposed therein forms the package (1); wherein the package (1) is sealed along a seal line (11*a*) such that the one or more absorbent articles are enclosed within an interior compartment of the bag (4); wherein the seal line (411*a*) on a front surface (414) of the bag (4) is substantially parallel to the bottom edge (420) of the bag (4) in a flat laid-out state; wherein length $L_S$ is the distance between the seal line (411*a*) and the top edge (448) along a direction parallel to the first side edge (422) of the bag (4) in a flat laid-out state; wherein $L_S$ is equal to or larger than 65 mm.

Example AB: The package of Example AA, wherein the package material forms the package (1) forming a front panel (14), a back panel (15) opposite the front panel (14), a first side panel (12), a second side panel (13) opposite the first side panel (12), a top panel (11), and a bottom panel (10) opposite the top panel (11), wherein the panels define an interior compartment of the package (1), and wherein one or more absorbent articles are disposed in the interior compartment.

Example AC: The package of Example AA or Example AB, wherein length $L_B$ is the distance between the bottom edge (420) and the top edge (448) along a direction parallel to the first side edge (422) of the bag (4) in a flat laid-out state and wherein the bag (4) has a front surface (414) and a back surface (415) and the front surface (414) and the back surface (415) have substantially the same length $L_B$.

Example AD: The package of any one of the Examples AA to AC, wherein length $L_P$ is the distance between the bottom edge (420) and the seal line (411*a*) along a direction parallel to the first side edge (422) of the bag (4) in a flat laid-out state; and wherein $L_S$ is from 0.50 to 1.00 times $L_P$, preferably from 0.60 to 0.95 times $L_P$, more preferably from 0.65 to 0.90 times $L_P$.

Example AE: The package of any one of the Examples AA to AD, wherein $L_S$ from 65 mm to 110 mm, preferably from 70 mm to 100 mm, more preferably from 75 mm to 95 mm.

Example AF: The package of any one of the Examples AA to AE, wherein the package (1) does not comprise wicketholes.

Example AG: The package of any one of the Examples AA to AF, wherein the package (1) is substantially free of holes.

Example AH: The package of any one of the Examples AA to AG, wherein the package material comprises at least 50 percent by weight natural fibers, preferably at least 70 percent by weight natural fibers, more preferably at least 90 percent by weight natural fibers.

Example AI: The package of any one of the Examples AA to AH, wherein all of the panels of the package comprise a unitary piece of package material.

Example AK: The package of any one of the Examples AA to AI, wherein the package material has a Basis Weight between about 50 gsm and about 120 gsm, preferably between about 55 gsm and about 115 gsm, more preferably between about 60 gsm and about 110 gsm, according to the Basis Weight Test Method.

Example AL: The package of any one of the Examples AA to AK, wherein the package material has a MD Tensile Strength of at least 5.0 kN/m, preferably at least 7.0 kN/m, more preferably at least 8.0 kN/m, according to the Strength Tensile Test Method.

Example AM: The package of any one of the Examples AA to AL, wherein the top panel comprises closing gussets (11*b*), a closing seam (11*a*), and a closing seam fin (11*c*) extending from the closing seam (11*a*).

Example AN: The package of any one of the Examples AA to AM, wherein the package material is recyclable, and wherein the package material exhibits a recyclable percentage of at least 70 percent, more preferably at least 80 percent, or most preferably at least 90 percent, as determined by PTS-RH:021/97 (Draft October 2019) method.

Example AO: The package of any one of the Examples AA to AN, wherein the package is formed from a single ply of the package material.

Example AP: The package of any one of the Examples AA to AO, wherein the package material is free of a barrier layer.

Example AQ: The package of any one of the Examples AA to AP, wherein the package material comprises a barrier layer.

Example AR: The package of any one of the Examples AA to AQ, wherein the barrier layer comprises polyethylene.

Example AS: The package of any one of the Examples AQ or AR, wherein the barrier layer forms less than 50 percent by weight of the package material, preferably less than 30 percent by weight of the package material, more preferably less than 10 percent by weight of the package material.

Example AT: The package of any one of the Examples AA to AS, wherein the bag (4) formed by the package material has a front surface (414) and a back surface (415) which are formed from a continuous package material web and are heat-sealed to one another along the first side edge (422) and second side edge (423).

Example BA: A process for forming a package for absorbent articles comprising the steps of a) providing a package material comprising natural fibers forming a bag (4) having a first side edge (422), a second side edge (423) opposite the first side edge (422), a top edge (448), and a bottom edge (420) opposite the top edge (448) in a flat laid-out state; the first side edge (422) and second side edge (423) are substantially parallel, the top edge (448) and bottom edge (420) are substantially parallel and the first side edge (422) and second side (423) edge are substantially rectangular to the top edge (448) and bottom edge (420) in a flat laid-out state; and having an inside facing surface and an outside facing surface, wherein the inside facing surface comprises a sealable material;

b) disposing one or more absorbent articles through an open end (48) located at the top edge (448) to the bag (4) to form a package (1) with an interior compartment defined by a front panel (14), a back panel (15) opposite the front panel (14), a first side panel (12), a second side panel (13) opposite the first side panel (12), a top panel (11), and a bottom panel (10) opposite the top panel (11) formed by the package material;

c) sealing the package along a seal line (11*a*) such that the one or more absorbent articles are enclosed within the interior compartment, wherein the seal line (411*a*) on a front surface (414) of the bag (4) is substantially parallel to the bottom edge (420) of the bag (4) in a flat laid-out state;

d) cutting the package along a trim line, which is located between the seal line and the top edge (448) and is substantially parallel to the seal line;

e) removing the trim piece corresponding to the cut part.

Example BB: The process of Example BA, wherein step c) is performed before step d).

Example BC: The process of Example BA, wherein step d) is performed before step c).

Example BD: The process of Example BA, wherein steps c) and d) are performed in parallel.

Example BD: The process of any one of Examples BA to BD, wherein $L_T$ is the distance between the top edge (448) and the trim line along a direction parallel to the first side edge (422) of the bag in a flat laid-out state; and wherein $L_T$ is equal to or larger than 0.80 times $L_S$.

Example BE: The process of any one of the Examples BA to BD, wherein $L_S$ from 65 mm to 110 mm, preferably from 70 mm to 100 mm, more preferably from 75 mm to 95 mm.

Example BF: The process of any one of the Examples BA to BE, wherein the package (1) does not comprise wicket-holes.

Example BG: The process of any one of the Examples BA to BF, wherein the package (1) is substantially free of holes.

Example BH: The process of any one of the Examples BA to BG, wherein the package material comprises at least 50 percent by weight natural fibers, preferably at least 70 percent by weight natural fibers, more preferably at least 90 percent by weight natural fibers.

Example BI: The process of any one of the Examples BA to BH, wherein all of the panels of the package comprise a unitary piece of package material.

Example BK: The process of any one of the Examples BA to BI, wherein the package material has a Basis Weight between about 50 gsm and about 120 gsm, preferably between about 55 gsm and about 115 gsm, more preferably between about 60 gsm and about 110 gsm, according to the Basis Weight Test Method.

Example BL: The process of any one of the Examples BA to BK, wherein the package material has a MD Tensile Strength of at least 5.0 kN/m, preferably at least 7.0 kN/m, more preferably at least 8.0 kN/m, according to the Strength Tensile Test Method.

Example BM: The process of any one of the Examples BA to BL, wherein the top panel comprises closing gussets (11*b*), a closing seam (11*a*), and a closing seam fin (11*c*) extending from the closing seam (11*a*).

Example BN: The process of any one of the Examples BA to BM, wherein the package material is recyclable, and wherein the package material exhibits a recyclable percentage of at least 70 percent, more preferably at least 80 percent, or most preferably at least 90 percent, as determined by PTS-RH:021/97 (Draft October 2019) method.

Example BO: The process of any one of the Examples BA to BN, wherein the package is formed from a single ply of the package material.

Example BP: The process of any one of the Examples BA to BO, wherein the package material is free of a barrier layer.

Example BQ: The process of any one of the Examples BA to BP, wherein the package material comprises a barrier layer.

Example BR: The process of any one of the Examples BA to BQ, wherein the barrier layer comprises polyethylene.

Example BS: The process of any one of the Examples BQ or BR, wherein the barrier layer forms less than 50 percent by weight of the package material, preferably less than 30 percent by weight of the package material, more preferably less than 10 percent by weight of the package material.

Example BT: The process of any one of the Examples BA to BS, wherein the bag (4) formed by the package material has a front surface (414) and a back surface (415) which are formed from a continuous package material web and are heat-sealed to one another along the first side edge (422) and second side edge (423).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package for absorbent articles comprising:

a package material comprising natural fibers;

wherein the package material forms a bag having a first side edge, a second side edge opposite the first side edge, a first top edge, a second top edge, and a bottom edge opposite the top edge in a flat laid-out state; the first side edge and the second side edge are substantially parallel, the top edge and the bottom edge are substantially parallel, and the first side edge and the second side edge are substantially rectangular to the top edge and the bottom edge in a flat laid-out state;

wherein the bag with one or more absorbent articles disposed therein forms the package;

wherein the package is sealed along a seal line such that the one or more absorbent articles are enclosed within an interior compartment of the bag;

wherein the seal line on a front surface of the bag is substantially parallel to the bottom edge of the bag in a flat laid-out state;

wherein the bag comprises a length $L_S$, wherein the length $L_S$ is the distance between the seal line and the top edge along a direction parallel to the first side edge of the bag in a flat laid-out state;

wherein $L_S$ is equal to or larger than 65 mm;

wherein the seal line is located substantially equidistant between the first top edge and the second top edge;

wherein the package material comprises less than about 5 percent, by weight of the package material, of inks, dyes, adhesives, and/or coatings;

wherein the package material comprises a total rejection percentage of from about 0.5 percent to about 40 percent; and wherein the package does not comprise wicket-holes.

2. The package of claim 1, wherein the package material forms the package forming a front panel, a back panel opposite the front panel, a first side panel, a second side panel opposite the first side panel, a top panel, and a bottom panel opposite the top panel, wherein the panels define an interior compartment of the package, and wherein one or more absorbent articles are disposed in the interior compartment.

3. The package of claim 2, wherein at least a portion of the seal line formed by the first side panel and the second side panel comprises a V-shape.

4. The package of claim 2, wherein the top panel comprises closing gussets.

5. The package of claim 1, wherein the package material comprises at least 50 percent by weight natural fibers.

6. The package of claim 1, wherein the bag comprises a length $L_P$, wherein the length $L_P$ is the distance between the bottom edge and the seal line along a direction parallel to the first side edge of the bag in a flat laid-out state; and wherein $L_S$ is from about 0.50 to about 1.00 times $L_P$.

7. The package of claim 1, wherein the length $L_S$ is from about 65 mm to about 110 mm.

8. The package of claim 2, wherein all of the panels of the package comprise a unitary piece of package material.

9. The package of claim 1, wherein the package material has a Basis Weight between about 50 gsm and about 120 gsm, according to the Basis Weight Test Method.

10. The package of claim 1, wherein the package material has a MD Tensile Strength of at least 5.0 kN/m, according to the Strength Tensile Test Method.

11. The package of claim 1, wherein the bag formed by the package material has a front surface and a back surface which are formed from a continuous package material web and are heat-sealed to one another along the first side edge and the second side edge.

12. The package of claim 1, wherein the package material is recyclable, and wherein the package material exhibits a recyclable percentage of at least 70 percent, as determined by PTS-RH: 021/97 (Draft October 2019) method.

13. The package of claim 1, wherein the package is formed from a single ply of the package material.

14. The package of claim 1, wherein the package material is free of a barrier layer.

15. The package of claim 1, wherein the package material comprises a barrier layer.

16. The package of claim 15, wherein the barrier layer comprises polyethylene.

17. The package of claim 15, wherein the barrier layer forms less than 50 percent by weight of the package material.

* * * * *